(12) United States Patent
Duhr et al.

(10) Patent No.: US 8,941,080 B2
(45) Date of Patent: Jan. 27, 2015

(54) METHOD AND DEVICE FOR PARTICLE ANALYSIS USING THERMOPHORESIS

(75) Inventors: Stefan Duhr, Munich (DE); Philipp Baaske, Munich (DE); Dieter Braun, München (DE); Christoph Jens Wienken, Kissing (DE)

(73) Assignee: Ludwig-Maximilians-Universitat Munchen, Munich (DE)

( * ) Notice: Subject to any disclaimer, the term of this patent is extended or adjusted under 35 U.S.C. 154(b) by 236 days.

(21) Appl. No.: 12/993,789

(22) PCT Filed: May 20, 2009

(86) PCT No.: PCT/EP2009/056162
§ 371 (c)(1),
(2), (4) Date: Dec. 20, 2010

(87) PCT Pub. No.: WO2009/141390
PCT Pub. Date: Nov. 26, 2009

(65) Prior Publication Data
US 2011/0084218 A1   Apr. 14, 2011

(30) Foreign Application Priority Data
May 20, 2008   (EP) ..................... 08009275

(51) Int. Cl.
*G01N 21/71*   (2006.01)
*G01N 21/17*   (2006.01)
(Continued)

(52) U.S. Cl.
CPC ............ *G01N 21/1717* (2013.01); *B01L 3/508* (2013.01); *G01N 15/1463* (2013.01);
(Continued)

(58) Field of Classification Search
CPC ................. G01N 21/171; G01N 21/64; B01L 2400/0451
USPC ....................................... 250/459.1
See application file for complete search history.

(56) References Cited

U.S. PATENT DOCUMENTS 5,255,976 A * 10/1993 Connelly .................... 374/31
6,850,363 B1 * 2/2005 Wendenburg et al. ........ 359/385
(Continued)

FOREIGN PATENT DOCUMENTS

GB   2 432 906   6/2007

OTHER PUBLICATIONS

Braun, et al. "Trapping of DNA by Thermophoretic Depletion and Convection", Physical Review Letters, Oct. 28, 2002, vol. 89, No. 18, pp. 188103-1 to 188103-4.
(Continued)

*Primary Examiner* — Marcus Taningco
(74) *Attorney, Agent, or Firm* — Foley & Lardner LLP

(57) ABSTRACT

The present invention pertains to a device and method to measure thermo-optical, preferably thermophoretic, characteristics of particles in a solution. The method comprises the steps of: (a) providing a sample probe comprising marked particles in a solution; (b) providing a temperature control system for creating a temperature gradient within said sample probe by contact heating, electrical heating and/or cooling; (c) detecting the marked particles at a first time; (d) creating a temperature gradient within the sample probe by means of the temperature control system; (e) detecting the marked particles in the sample probe at a, preferably predetermined, second time and/or at a predetermined location within the temperature gradient, and (f) characterizing the particles based on said two detections.

41 Claims, 12 Drawing Sheets

(51) Int. Cl.
*B01L 3/00* (2006.01)
*G01N 15/14* (2006.01)
*G01N 21/64* (2006.01)
*G01N 15/00* (2006.01)
*G01N 15/10* (2006.01)
*G01N 35/00* (2006.01)

(52) U.S. Cl.
CPC .......... *G01N21/171* (2013.01); *G01N 21/6408* (2013.01); *G01N 21/6428* (2013.01); *G01N 21/6458* (2013.01); *G01N 21/648* (2013.01); *B01L 2300/041* (2013.01); *B01L 2300/046* (2013.01); *B01L 2300/0822* (2013.01); *B01L 2300/1805* (2013.01); *G01N 2015/0038* (2013.01); *G01N 2015/1075* (2013.01); *G01N 2015/1497* (2013.01); *G01N 2021/1731* (2013.01); *G01N 2035/00356* (2013.01)
USPC ...................................................... 250/459.1

(56) References Cited

U.S. PATENT DOCUMENTS

2002/0195342 A1* 12/2002 Lee et al. ...................... 204/451
2003/0077599 A1* 4/2003 Sogard .............................. 435/6
2004/0161767 A1* 8/2004 Baldwin et al. ................... 435/6
2005/0054081 A1* 3/2005 Hassard et al. ............ 435/287.2

OTHER PUBLICATIONS

Chan, et al. "Soret Coefficients for Aqueous Polyethylene Glycol Solutions and Some Tests of the Segmental Model of Polymer Thermal Diffusion", Journal of Solution Chemistry, Mar. 2003, vol. 32, No. 3, pp. 197-214.
Crane, et al. "DNA mutation detection via fluorescence imaging in a spatial thermal gradient, capillary electrophoresis system", Review of Scientific Instruments, Nov. 2001, vol. 72, No. 11, pp. 4245-4251.
Duhr, et al. "Thermophoresis of DNA determined by microfluidic fluorescence", The European Physical Journal E, 2004, vol. 15, pp. 277-286.
Duhr, et al. "Why molecules move along a temperature gradient", PNAS, Dec. 26, 2006, vol. 103, No. 52, pp. 19678-19682.
International Search Report in PCT/EP2009/056162 dated Oct. 22, 2009.
Ramos, et al. "AC electrokinetics: a review of forces in microelectrode structures", J. Phys. D: Appl. Phys., 1998, vol. 31, pp. 2338-2353.
Rathore, A. "Joule heating and determination of temperature in capillary electrophoresis and capillary electrochromatography columns", Journal of Chromatography A., 2004, vol. 1037, pp. 431-443.
Schimpf, et al. "Characterization of Thermal Diffusion in Polymer Solutions by Thermal Field-Flow Fractionation: Effects of Molecular Weight and Branching", Macromolecules, 1987, vol. 20, pp. 1561-1563.

* cited by examiner

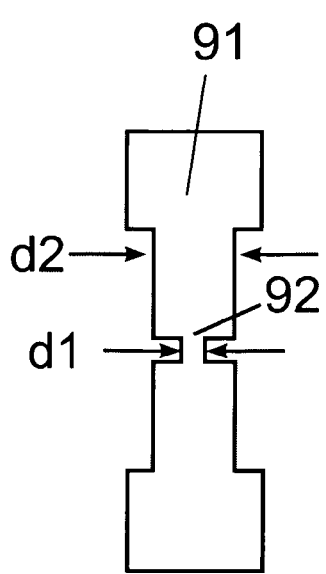
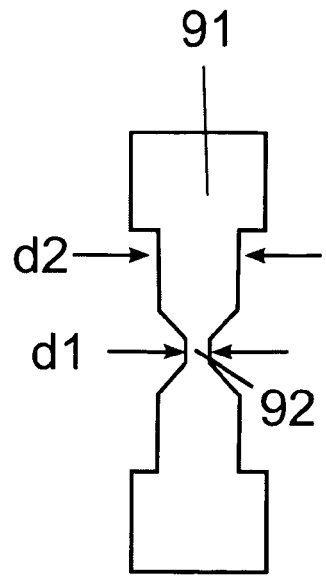
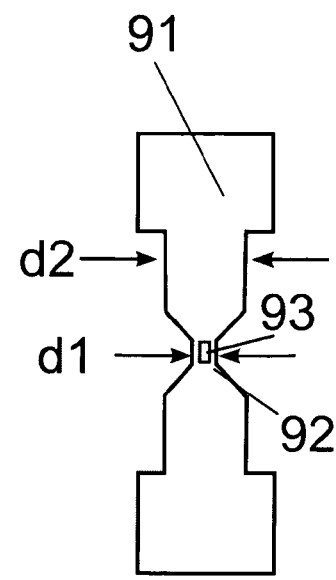
Fig. 6a          Fig. 6b          Fig. 6c
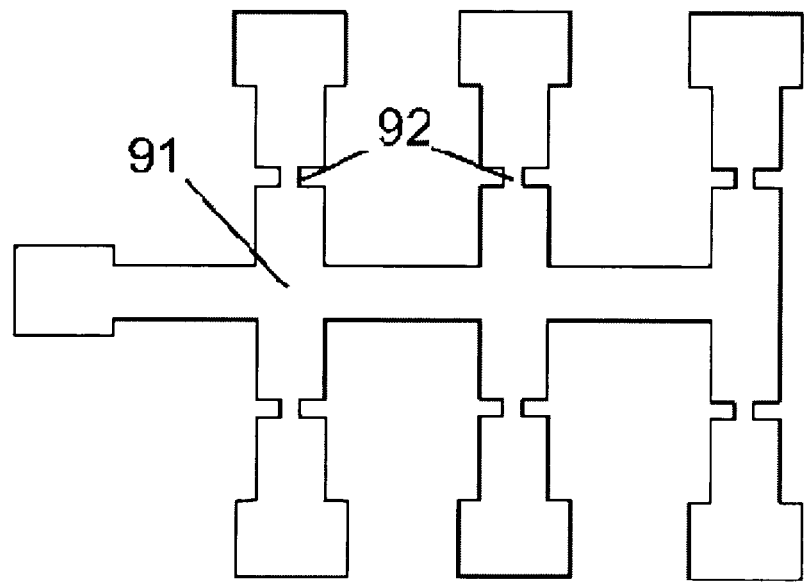
Fig. 6d

METHOD AND DEVICE FOR PARTICLE ANALYSIS USING THERMOPHORESIS

CROSS-REFERENCE TO RELATED PATENT APPLICATIONS

This application is the U.S. National Phase of PCT/EP2009/056162, filed May 20, 2009, which claims priority from European Patent Application No.: EP 08009275.2, filed May 20, 2008, all of which are incorporated herein by reference in entirety.

The present invention relates to a method, device and its use for thermo-optical characterisation of particles. In particular, the present invention relates to a method and an apparatus for measuring the surface properties of small, particles (e.g. submicron to µm scale) with thermophoresis. The present invention also relates to a method and apparatus for analyzing the physical and chemical properties of small particles and/or changes in these properties. More particularly, the invention uses thermophoresis in a created spatial temperature gradient, combined with optical detection. Moreover, the present invention relates to a method and a device to measure characteristics, preferably size and surface properties, of molecules, like biomolecules, the interaction of molecules, particularly biomolecules with, e.g. further (bio)molecules, particularly modified biomolecules, particles, e.g. nanoparticles/ions or microparticles, beads, e.g. microbeads and/or the determination of the length/size (e.g. hydrodynamic radius) of individual molecules, particularly of biomolecules, of particles (e.g. nanoparticles, microparticles), or of beads (e.g. microbeads) as well as the determination of e.g. length or size (e.g. hydrodynamic radius) of (bio)molecules or particles. Also combinations of these characteristics may be determined with the means, uses and methods of this invention. It is of note that, the present invention is, however, not limited to the measurement characterization of biomolecules. Therefore, also the characteristics of other compounds/particles can be measured and determined by the means, and methods disclosed herein, for example kinetic events and interactions of molecules may be determined and/or measured. Accordingly, also chemical reactions (like inorganic or organic reactions) may be measured by the methods and under use of the devices of the present invention. It is also envisaged to determine, complex formations and/or their dissociation. The method of the present invention applies to polar (e.g. water, ethanol, acetonitril-), non-polar (organic) solvents (e.g. hexane, toluene), emulsions (e.g. milk), foams and the like.

It has been a longstanding desire to provide systems and methods for accurately detecting the size and surface properties of small particles e.g. DNA, Proteins and/or other artificial/non-artificial micro/nanoparticles (e.g. titanium oxide, soot particles, pigments in non aqueous solutions and more).

Normally, the size of small particles and/or their surface properties are detected by light scattering, electrophoresis or dielectrophoresis or more exotic techniques like Temperature gradient gel electrophoresis, described, e.g. in German Application DE-OS 36 22 591. Although some of these methods are widespread nowadays they suffer from many disadvantages.

So the use of electrophoresis is limited to charged panicles and needs time consuming preparation before the actual measurement. Further, electrophoresis is hard to miniaturize due to electrochemical effects at the metal-buffer interface.

Many of these methods are limited to one specific measurement variable of the tested particle, e.g. a size/charge ratio for electrophoresis or just the size for light scattering experiments. Thus, it is difficult to detect any change in the particles' surface properties except surface charges.

Besides these analyses of particle properties it is often of interest to detect the interaction of particles with a binding partner, e.g. protein-protein interaction like antibodies with antigens, molecules with proteins or DNA strands with proteins. These high sensitive detections are often performed using enzyme-linked immunosorbent assays (ELISA). But ELISA needs complicated constructs comprising antibodies and enzymes, in part bound to a surface to visualize the presence of the proteins or particles of interest. Thus ELISA experiments need laborious preparations or expensive commercial substrates.

Duhr et al. in European. Phys. J. E 15; 277, 2004 relates to "Thermophoresis of DNA determined by microfluidic fluorescence" and makes use of thermophoretic driving forces in miniaturized biotechnology devices. This article discusses an all-optical approach in thin micro fluids to measure and apply thermophoresis for biomolecules in small volumes and aqueous solutions, i.e. both the creation of the temperature gradient and the detection are based on an optical, method. This all-optical method is only suitable for solutions mainly consisting of water. The method cannot be applied to solutions which mainly consist of a non aqueous solvent (e.g. oil, toluene, etc.).

The temperatures are measured with high spatial resolution by the temperature sensitive fluorescence of a fluorescent dye. Typically, one measurement according to Duhr et al. (2004, loc. cit.) takes 300 s or even more. It is further speculated in Duhr et al. (2004, loc. cit.), that the movement of polymers, in particular DNA, in a temperature gradient is independent of the chain length of the molecule, an assumption in line with theoretical considerations, see e.g. Braun and Libchaber, Physical Review Letters 89, 18 (2002). This assumption strongly confines thermo-optical characterization of molecules based on thermophoresis, since the technique would solely be dependent on changes in size of molecules and would exhibit no sensitivity to surface properties.

Moreover, as indicated above, this method is limited to use of solutions mainly consisting of water. It cannot be used with solutions mainly comprising a non aqueous solvent, such as oil, toluene or the like.

In contrast to standard detecting techniques the use of thermophoresis as a discriminating force allows circumventing these limitations. This technique is used in Duhr et al. (PNAS 103, 19678-19682 (2006)) where a thermophoretic approach is used to determine particle properties or binding of molecules to tagged partners. Also measuring of Antigen-Antibody interactions. Protein-Protein interactions or other surface modifications is possible with this technique.

These measurements are also performed all optical in a fluid chamber using an infrared (IR) laser to heat an aqueous solution highly localized while the detection of the resulting thermophoretic movement is observed using standard imaging techniques, like fluorescence microscopy.

Although these thermophoretic measurements offer a great variety of new possibilities they suffer from their complex structure and the relatively high price for IR heating laser. In addition the method is limited to a few solvents which absorb the light emitted from the IR laser.

It is therefore an object of the present invention to provide an improved method and device for a thermo-optically characterisation of particles or molecules, in particular which overcome the disadvantages of the prior art. It is a further or additional object underlying the present invention, to provide a method and device which can be used in a wide variety of applications, which are easy and efficient to handle and to manufacture, which are robust and/or which provide reliable results.

These and other objects are achieved by the features of the independent claims. Further preferred embodiments are characterized in the dependent claims.

SUMMARY OF THE INVENTION

The present invention allows using all the advantages of a thermophoretic measurement of particles, particles' properties and/or changes in particle properties and circumvents the disadvantages such as the high costs of the setup known from the art and limitations on the liquids which can be heated.

The method of the present invention particularly allows thermo-optical measurements of parameters/characteristics such as size and surface properties, charge, conformation of a molecule, shape of a molecule, chemical groups on the surface, inter/intramolecular interactions, conformation of molecule, small molecule/ion binding to molecules and interaction between biomolecules or biomolecules and particles/nanocrystals/microbeads with a simple, efficient, robust and reliable method/apparatus. In particular, the present invention allows an automated measurement with an improved through-put within improved time spans.

Also the present invention circumvents the need that laser radiation has to be absorbed by the solvent, an obstacle limiting the use of IR heating lasers to aqueous solutions. The present invention may be used with different polar and non-polar solvents, preferably a great variety of matter in the liquid phase may be used, e.g. molten, materials (e.g. polymer melts) or Liquid Crystals (e.g. in the nematic phase). Also mixtures of all mentioned and other liquids and solvents may be used with the present, invention.

In the context of this invention, in particular the claims, it is noted that, the terms "particle" or "particles" also relate to beads and/or microparticles, particularly microbeads, nanoparticles or molecules, particularly biomolecules, e.g. nucleic acids (such as DNA, RNA, LNA, PNA), proteins and other biopolymers as well as biological cells (e.g. bacterial or eukaryotic cells) or sub-cellular fragments, viral particles or viruses and cellular organelles and the like or inorganic compounds. In the context of the present invention, a nanoparticle is a microscopic panicle with at least one dimension less than 190 nm and a microparticle/microbead is a microscopic particle/bead which has a characteristic dimension of less than 1 mm but normally more than 100 nm. The term "modified particle" or "modified bead" relates in particular to beads or particles which comprise or are linked to molecules, preferably biomolecules. This also comprises coating of such beads or particles with these molecules or biomolecules.

Although the particles mentioned above are mainly biomolecules the invention is not limited to an application, of biomolecules but allows also measuring.

The present invention provides means and methods for the thermo-optical measurements and/or thermo-optical characterization of particles or molecules, in particular biomolecules, by the measurements and/or the detection of differences in the thermo-optical properties. Their thermo-optical properties mainly originate from differences in thermophoretic mobility DT (e.g. the velocity of particles/molecules in a temperature gradient). In particular, the detected signal is dependent on the thermophoretic mobility $c/c_0 = \exp[-D_T/D)(T-T_0)]$, with the diffusion coefficient D, concentration c and temperature T. A DT independent of the polymer length as expected from Duhr (2004; loc. cit.) and others (e.g. Chan et al. Journal of Solution Chemistry 32, 3 (2003); Schimpf et al. Macromolecules 20, 1561-1563 (1987)) would render the analytics of biopolymers like DNA and proteins almost impossible since only changes in the diffusion constant would contribute to the thermo-optical properties, which are minute in most cases.

Thermo-optical characterization in accordance with this invention is based on the creation of temperature gradients at small length scales in a solution. The solution may be an aqueous solution but also a solution where the solvent is non-aqueous, for example non-polar (e.g. hexane). By doing so, the energetic states of the molecules in the solution are changed depending on the temperature and the properties of the molecule, i.e. the molecules experience a spatial potential originating from the spatial differences in temperature. This potential drives a directed motion of molecules along the temperature gradient an effect called thermophoresis.

In other words, in this temperature profile particles move due to thermophoresis and establish a concentration profile. After a given time, depending on, i.a., the chamber dimensions and the particle's diffusion coefficient the steady-state distribution is reached. The diffusion time is hereby very sensitive to the chambers dimension as it contributes quadratically while the diffusion coefficient contributes only linearly. When the temperature control system is switched off the concentration gradient equilibrates and the particles diffuse back. The complete dynamics are preferably observed using microscopy techniques e.g. fluorescence microscopy.

With the present invention, thermophoresis is observed at times in a range from about 0.01 seconds to 30 minutes, preferably 0.01 seconds to 10 minutes, preferably 1 second to 5 minutes, preferably 60 second to 5 minutes Thermophoresis is a method which is sensible to surface properties of molecules in a solution. It is not necessary to expose molecules to a different matrix (like in chromatography) or to interact with the molecules physically in any way (e.g. by direct contact or by adding substances). Only interactions within a temperature gradient are necessary. Heating and/or cooling elements are used for manipulation of matter by creating spatial temperature distribution and fluorescence, is preferred to detect molecules.

The gist of thermo-optical or thermophoretic characterization based on thermophoresis as provided herein is that differences in thermophoretic mobility (i.e. the velocity of molecules in a temperature gradient) and hydrodynamic radius can be detected by analyzing the spatial distribution of concentration (i.e. by the spatial distribution of e.g. fluorescence) or the fluctuations of single particles trapped in the spatial temperature profile. This embodiment is of particular relevance for the herein described thermo-optical trap for trapping particles, molecules, beads, cellular components, vesicles, liposomes, cells and the like. While the hydrodynamic radius is only related to the radius of a molecule, the thermophoretic mobility is sensitive to charge, surface properties (e.g. chemical groups on the surface), shape of a molecule (i.e. size of surface), conformation of a protein or interaction between biomolecules or biomolecules and particles/nanocrystals/microbeads. This means that if any of the mentioned properties are changed, the molecules will experience a different thermodynamical potential, resulting in differences in thermophoretic mobility (i.e. change in spatial concentration profile or fluctuation amplitude of trapped particles).

Thus, the present invention relates to thermally induced processes, e.g. temperature gradient induced directed motion of particles.

The approach according to the present invention differs from most state of the art analysis devices and methods where the generation of heat is an unwanted by-product. For dielectrophoresis the experimental results are corrected for temperature effects and it is tried to keep temperature effects negligible. (Ref: Ac electrokinetics: a review of forces in microelectrode structures A. Ramos et al 1998 J. Pays. D: Appl Phys. 31 2338-2353). For the widespread analysis method of electrophoresis Joule heating is titled to "plague electro-driven separations" and leads to separation inefficiencies. (Ref: Joule heating and determination of temperature in capillary electrophoresis and capillary electrochromatography columns, Anurag S. Rathore, Journal of Chromatography A, Volume 1037, Issues 1-2, 28 May 2004, Pages 431-443).

Moreover the spatial localization of the temperature distribution is an unwanted effect for state of the art micro-heating elements. For example micro-hotplates for gas analysis devices use heat distribution plates to obtain a uniform temperature over the whole area. The methods presented in this invention allow taking advantage of the temperature inhomogeneities and using it for the characterisation of panicles.

The thermo-optical characterization mentioned above provides the means for fast thermo-optical analysis of panicles and/or molecules, in particular for the thermo-optical characterisation of biomolecules, like nucleic acid molecules (e.g. DNA, RNA, PNAs or proteins and peptide analysis. This characterisation comprises, inter alia, size determination, length determination, determination of biophysical characteristics, like melting points or melting curves, complex formations, protein-protein interactions, protein or peptide folding/unfolding, of intra-molecular interactions, intermolecular interactions, the determination of interactions between particles or molecules, and the like. Prior art methods for detection and quantification of molecular interactions and characteristics, in particular biomolecular interactions and characteristics are very time consuming which means that the time needed for an analysis is on in the order of 30 minutes up to hours. In accordance with the present invention, the method and device allow advantageous parallelization so that the overall measurement times can be significantly reduced. Depending on the actual embodiment, one measurement may typically take less than 600 s, less than 300 s, less than 200 s, less than 100 s or even less than 50 s, which is clearly faster than the methods described in the prior art. The present invention can detect and quantify molecular interactions and characterisations, in particular biomolecular interactions and/or biochemical/biophysical properties within 1 second up to 10 minutes. The term interaction comprises interaction between biomolecules (e.g. protein, DMA, RNA, hyaluronic acids etc.) but also between (modified) (nano) particles/ions/(micro micro)beads and biomolecules. In this context, modified particles, molecules, biomolecules, nanoparticles, microparticles, beads or microbeads comprise fluorescently labelled particles, molecules, biomolecules, nanoparticles, microparticles, beads or microbeads. Fluorescently labelled particles, molecules, biomolecules, nanoparticles, microparticles, beads or microbeads may be e.g. particles, molecules, biomolecules, nanoparticles, microparticles, beads or microbeads, to which one or more fluorescent dyes have been attached, e.g. covalently attached. For example, the fluorescent dyes may be selected from the group of 6-carboxy-2',4,4',5',7,7'-hexachlorofluorescein. (6-HEX SE: C20091, Invitrogen). 6-JOE SE or 6-TET SE. In other cases, the intrinsic fluorescence of e.g. particles, molecules, biomolecules may be exploited according to the invention, e.g. the fluorescence properties of tryptophan, tyrosine or phenylalanine in a protein may be exploited. The terms "marked" and "labelled" are used synonymously in the context of this invention. In the context of this invention, "marked particles" particularly refer to luminescently, e.g., fluorescently labelled molecules/particles or other molecules/particles which can be detected by fluorescence means, e.g. molecules/particles comprising an intrinsic fluorophor, molecules/particles, comprising intercalating dyes or particles/molecules with fluorophores attached.

In short summary, the device and method according to the present invention make use of thermophoretic driven, forces in order to separate, deplete and/or accumulate particles of interest in a solution. Since thermophoretic forces are based on a spatial temperature gradient, the present invention uses a temperature control system for generating, or creating a sufficient temperature gradient, in particular, a temperature control system according to the present invention comprises one or a plurality of heating and/of cooling elements, in the following a non-limiting list of heating and/or cooling elements/devices, which may be used in order to create the desired temperature gradient, will be discussed in more detail. Desired temperature gradients lie within the range from about 0.001 K/µm to 20K/µm, preferably from 0.001K/µm to 5K/µm, more preferably from 0.01K/µm to 1K/µm and more preferably is about 0.05K/µm.

According to one embodiment of the invention, there is created a, preferably defined and/or adjustable, temperature gradient, preferably a spatial two-dimensional or three-dimensional temperature gradient, by means of contact temperature control including contact heating and/or contact cooling. In particular, the desired temperature gradient may be created within a sample probe by heating and/or cooling elements which are arranged in direct contact, with the sample probe and/or the measurement chamber. The temperature control can also be used to change the temperature gradient over time. In the contest of this invention, in particular the claims, it is noted that the terms "contact" heating or "direct contact" heating is to be interpreted in the sense of heat conduction, heat transfer and/or heat exchange. In other words, the two articles or elements x and y are in direct heating contact even if a material z is between the two articles x and y, as long as material z allows a transfer of thermal energy from article % through the material 2 to the article y via conduction and/or convection and vice versa. In particular, classical transfer of thermal energy occurs only through conduction, convection, radiation or any combination of these. Preferably, material z is not a gas or a gaseous medium. Preferably, the temperature control is not achieved by directly or solely exposing the sample probe to radiation, for heating and/or cooling the sample probe.

A typical heating element converts electricity, e.g. a current flow, into heat through, the process of Ohmic or Joule heating. Electrical current running through the element encounters resistance, resulting in heating of the element. In the following a non-limiting list of heating elements which may preferably be used with the invention will be briefly discussed, Bare wires or ribbons, either straight or coiled may be used. Any kind of printed metal/ceramic tracks deposited in/on the sample, probe or the measurement chamber may be used. Further examples for heating elements include: heating plates made of ITO (indium tin oxides layer or a transparent polymer and any other kind of material that is transparent and electrically conductive, microstructures made of electrically conductive material, which is not transparent e.g. gold, platinum, silver. The beating elements may either provide a homogeneous temperature distribution (i.e. to create to a 1-dimensional temperature distribution in z-direction) in a sample probe or measurement chamber or may be designed microstructured to provide a local spatial temperature distribution in selected areas/volumes of a sample probe or measurement chamber in two or three dimensions. The heating structures may be coated with an electric isolator (e.g. polymer, glass, etc) in order to suppress electrochemical reactions.

In order to create a temperature gradient within the sample probe, parts of the probe may be additionally or alternatively cooled by means of cooling elements such as, e.g., peltier elements, air cooling, and/or a water bath.

Alternatively or additionally, according to a former embodiment, the heating of the heating element described above can be performed optically using a material which absorbs light at a given wavelength of the illumination resulting in heating of the element. The heating effect is sufficient for example for a Nickel-Chromium layer irradiated with an IR-Laser. The heating of the heating element thus takes place outside the actual measurement chamber and without radiation heating the sample probe. Rather, the heat is conducted by direct contact heating of the measurement chamber and/or sample probe via the heating element.

Alternatively or additionally, according to another embodiment according to the present invention the electric current is used to heat the electrolyte itself instead of using, e.g., a wire of conducting material, thereby preferably creating a more localized heat distribution. As the resistance of the solution or sample probe is much lower than the resistance of the measurement chamber and/or the surrounding structure nearly all voltage drop occurs is the electrolyte. The structures preferably are in the regime of some microns but with a, preferably micron-sized, gap in between. Thus, the heating is constrained to a very small volume in x-y direction, i.e. the gap. Such heating is preferably understood as being encompassed, by the term contact heating within the present invention. Such heating, which is further discussed below, and which preferably makes use of a high frequency alternating current, is also referred to as electrical heating.

Alternatively or additionally, still another embodiment is based on the following. A DC-current through the electrolyte results in movement of charged particles which counteract the driving DC-current by building an electric field and thereby reducing the voltage applied at first. According to this embodiment these effects are circumvented by using high frequency alternating currents (AC). With the frequency chosen sufficiently high the ions and charge carrier in the sample cannot follow anymore and thus no counteracting electric fields can be established. By using high frequency alternating current the solution in between the electrodes is heated.

Preferably small micrometer-sized structures are used to obtain the capacitive heating of the sample. For highly localized heating spots the actual volume between the two electrodes is preferably small so the electrodes have a finger like structure with every ringer being only some microns wide.

For a higher localization of the heating profile various layouts of the finger structure are used in the different embodiments. The finger structure which preferably tapers towards the heated gap allows focusing the heating spot in a more narrow profile.

With the above preferred heating/cooling elements, it is possible to create spatial, i.e. two-dimensional or three-dimensional (2D, 3D), temperature distributions and/or gradient, comprising the desired temperatures, within the sample probe. Both, local temperature distributions and temperature gradients, can be used as described below to measure parameters, in particular biomolecular parameters. In a particular embodiment, the temperature distribution or gradient is created on small scales, e.g. on mm scale or even micrometer scale. This may be advantageous since strong temperature gradients on small scales shorten the time the system needs to equilibrate (i.e. measurement time). In particular embodiments, it is advantageous to create the spatial temperature distribution on a length scale of less than 1 μm.

As mentioned above, the effect of separation, depletion and/or accumulation of particles on the basis of thermophoretic effects is dependent on the particle properties such as the surface properties, charge, size, and/or the solvent (buffer). By detecting or measuring the degree of separation, depletion and/or accumulation in dependency of the created temperature gradient, a characterization of the particles is possible. In the following a non-limiting list of preferred detection devices and techniques will be discussed in detail.

According to a preferred embodiment the sample probe comprises marked particles/molecules in a solution. The marked, particles may be excited luminescently, preferably fluorescently (also intrinsic fluorescence, e.g., tryptophan, in case of proteins) and the excitation of the marked particles is detected at a first and second time, preferably before and after the thermophoretic movement is induced. Without differing from the gist of the invention it is also envisaged to a person skilled in the art that instead of detection based on luminescence (or fluorescence) other detection methods are possible. Depending on the size and properties of the particles to be detected, the step of fluorescently exciting may be omitted, and detection based on light scattering, Raleigh Scattering, (UV) absorption, phase contrast, phosphorescence and/or polarisation are possible. Moreover, for particles larger than 100 nm, the movement of such particles can be detected by single particle tracking.

In particular, detection according to the present invention may be based on transmitting fluorescence systems, epi-fluorescence, TIRF, confocal detection, detection with a limited depth of field (DOF), a microscope with, a narrow z-focus and/or electrical detection methods.

Epifluorescence is an optical set-up for a fluorescence microscope in which the objective lens is preferably used both to focus excitation light (preferably ultraviolet light) on the sample probe and collect from the sample probe (e.g. fluorescent light). Epifluorescence is more efficient than transmitted fluorescence, in which a separate lens or condenser is used to focus ultraviolet light on the sample probe. Epifluorescence also allows fluorescence microscopy to be combined with another type on the same microscope. The key to the optics in an epifluorescence microscope is the separation of the illumination (excitation) light from the fluorescence emission emanating from the sample. In order to obtain either an image of the emission without excessive background illumination, or a measurement of the fluorescence emission without background "noise", the optical elements used to separate these two light components must be very efficient.

In a conventional (i.e., wide-field) fluorescence microscope and/or epifluorescence, the entire sample probe is flooded in light from a light source. Due to the conservation of light intensity transportation, all parts of the sample probe throughout the optical path will be excited and the fluorescence detected by a detector or a camera. In contrast, a confocal microscope uses point illumination and a pinhole in an optically conjugate plane in front of the detector to eliminate out-of-focus information. Preferably, only the light within the focal plane will be detected, so the image quality is much better than that of wide-field images. As only one point is illuminated at a time in confocal microscopy, 2D or 3D imaging requires scanning over a regular raster (i.e. a rectangular pattern of parallel scanning lines) in the sample probe. The thickness of the focal plane is defined mostly by the square of the numerical aperture of the objective lens, and also by the optical properties of the sample probe and the ambient, index of refraction.

Another technique by which substantially only the light emitted from the focal plane is used for the detection will be called in the following; "microscope with a narrow z-focus" or detection with a narrow depth of field. In particular, the depth of field (DOF) is the portion of a scene that appears sharp in an image. Although a lens can precisely focus at only one distance, the decrease in sharpness is gradual on either side of the focused distance, in contrast to the confocal method described above, the substantially whole sample is illuminated, whereas only the information of the focal plane is used for the detection.

According to still another preferred embodiment, the detection may be based on TIRF. A total internal reflection fluorescence (TIRF) microscope is a type of microscope with which a thin region of a sample probe, usually less than 200 nm, can be observed. A TIRF microscope uses evanescent waves to selectively illuminate and excite fluorophores in a restricted region of the sample probe immediately adjacent to the measurement chamber-solution interface (e.g. a material-liquid (glass-water) interface). Evanescent waves are generated only when the incident light is totally reflected at the measurement chamber-solution interface. The evanescent electromagnetic field decays exponentially from the interface, and thus penetrates to a depth of only approximately 100 nm into the sample medium. Thus the TIRF microscope enables a selective visualization of surface regions. TIRF can also be used to observe the fluorescence of a single molecule, making it an important tool of biophysics and quantitative biology.

The thermo-optical characterization in accordance with this invention allows determining properties of molecules or particles in solutions, in particular in both aqueous and in non aqueous (e.g. organic) solutions. It also allows discriminating, between different conformations of one particle or molecule species and it also allows discriminating between different species of particles or different molecules. The characterization can be used in all cases where the particles show a response to the temperature gradient and changes in the absolute, temperature. An advantageous feature of the present invention is the presence of a defined spatial temperature distribution. In particular, the temperature distribution is generated locally on small length scales, e.g. on cm, mm or even microscopic length scales by local contact heating with heating and/or cooling element. Another advantageous feature is that the response of the particles or molecules is assigned to a certain place of the known, optically generated spatial temperature distribution. Accordingly, temperature, place and response of the particles are directly correlated.

According to a preferred embodiment, the device is designed with a plurality, e.g., 2, 4, 8, 20 or more, contact heating means which allow simultaneous heating of a plurality of sample probes. Preferably, a control unit provided that allows sequential, synchronous and/or parallel individual control of the heating means to create a plurality of temperature gradients in the plurality of sample probes. These temperature gradients may be different gradients or equal gradients. Preferably, the detection means is adapted to screen and thus subsequently perform the detection step(s). Preferably, detection and heating are synchronised in order to allow proper detection at first, second, and/or third, preferably predetermined, times for each individual sample probe. Additionally or alternatively, the detection is performed in sequential and/or parallel for a number of measurement chambers or sample probes. The present invention, as also further discussed below, is of particular advantage vis-à-vis the prior art. In particular, the present invention provides an effective and efficient method and device for thermo-optical characterization of particles, which is easy to handle and perform, easy and cheap to set up, is robust and provides reliable results and allows a variety of uses and of materials to be used with the present invention. Moreover, the present invention allows an improvement in throughput in that the invention allows the parallel heating of multiple sample-probes and, e.g., simultaneous, e.g., linear detection by means of, e.g., one detection unit.

In addition or alternatively to the above discussed features and embodiments, the present invention preferably relates to the following aspects;

1. Method to measure thermo-optical, preferably thermophoretic, characteristics of particles in a solution comprising, preferably in this order, the steps of;
   (a) providing a sample probe comprising marked particles in a solution;
   (b) providing a temperature control system for creating a temperature gradient within said sample probe by contact heating, electrical heating and/or cooling;
   (c) detecting the marked particles;
   (d) creating a temperature gradient, within the sample probe by means of the temperature control system;
   (e) detecting the marked panicles in the sample probe at a, preferably predetermined, further time and/or at a predetermined location within the temperature gradient, and
   (f) characterizing the particles based on said two detections.
2. Method according to aspect 1, wherein the method comprises the step of performing a further detection at a, preferably predetermined, further time.
3. Method according to aspect 1, 2, wherein the second and/or detection time is while and/or after heating, particularly in order to measure back diffusion.
4. Method according to aspect 1, 2 or 3, wherein times of one or more of the three detections are predetermined times, preferably depending on absolute time, the completion or conduction of further method steps, and/or relative time between the two times,
5. Method according to any one of the preceding aspects, further comprising the step of exciting luminescence, preferably fluorescence, of said marked particles wherein the detection steps comprise detecting luminescence, preferably fluorescence, of said excited particles,
6. Method according to any one of the preceding aspects, wherein the temperature control system controls the temperature by at least one heating and/or cooling means using one or more of a wire, a Peltier element, a plate, a conductive path, means for creating a high frequency electric field in the sample probe, art indium-oxide (ITO) element and/or means with a radiation absorbing surface.
7. Method according to any one of the preceding aspects, wherein detection is performed by use of one or more of epifluorescence (EPI) microscope, total internal reflection fluorescence (TIRF) microscope, confocal microscope, CCD, APD, PMT, and/or a microscope.
8. Method according to any one of the preceding aspects, wherein the temperature gradient lies in the range from about 0K/μm to 20K/μm, preferably from 0.001K/μm to 5K/μm, more preferably from 0.01K/μm to 1K/μm and more preferably is about 0.05K/μm,
9. Method according to any one of the preceding aspects, wherein the temperature, increase in the sample probe lies in the range from about 0° C. to 100° C., preferably from 2° C. to 50° C. and more preferably from 5° C. to 20° C.

10. Method according to any one of the preceding aspects, wherein the sample probe volume lies in the range from about 1 pl to 100 μl, preferably from 0.1 μl to 30 μl and also preferably from 0.5 μl to 5 μl 11. Method according to any one of the preceding aspects, wherein the time span between the first time and the second time lies in the range from, about 1 us to 60 min, preferably about 0.01 sec to 20 min. preferably about 1 sec to 10 min preferably 60 sec to 5 mm.

12. Method according to any one of the preceding aspects, wherein the predetermined location within the temperature gradient is at the surface, the bottom, the side of a measurement chamber and/or the sample probe and/or at a predetermined distance from heating and/or cooling means or at a place of specific temperature, preferably close to the heating and/or cooling means in a region of high temperature gradients.

13. Method according to any one of the preceding aspects, wherein a plurality of sample probes are measured subsequently and/or in parallel.

14. A device for measuring thermo-optical, preferably thermophoretic, characteristics of particles in a solution, in particular according to a method of any one of aspects 1 to 13, the device comprises:
a measurement chamber for receiving a sample probe containing marked panicles in a solution;
means for detecting the marked particles in the sample probe;
a temperature control system, for creating a temperature gradient within said sample probe by contact heating and/or cooling, and
a control means adapted for controlling said detection means to detect said marked particles at a first time and for controlling said detection means and temperature control system to detect said marked particles in the sample probe at a second time and/or at a predetermined location within, a temperature gradient created by the temperature control system.

15. Device according to aspect 14, wherein the control means is adapted to control the first and/or second times to be predetermined times, preferably depending on absolute time, the completion or conduction of further method steps and/or relative time between the two times.

16. Device according to aspect 14 or 15, further comprising means for exciting luminescence, preferably fluorescence, of said marked particles wherein the detection means is adapted to detect luminescence, preferably fluorescence, of said excited particles.

17. Device according to aspect 14, 15 or 16, wherein the temperature control system comprises one or more of each or more of the following heating and/or cooling means; a wire, a Peltier element a plate, a conductive path, means for creating a high frequency electric field, an indium-tin-oxide (TTO) element and/or means with a radiation absorbing surface for controlling the temperature.

18. Device according to any one of aspects 14 to 17, wherein the detection means comprises one or more of epifluorescence (EPI) microscope, total internal reflection fluorescence (TIRF) microscope, confocal microscope. CCD, APD, PMT, and/or a microscope.

19. Device according to any one of aspects 14 to 18, wherein the device comprises means for characterizing the particles based on said at least two detections.

20. Device according to any one of aspects 14 to 19, wherein the temperature control system is adapted to create a temperature gradient lying in the range from about 0K to 20K, preferably from 0.001K/μm to 5K/μm, more preferably from 0.01K to 1K/μm and more preferably is about 0.05K.

21. Device according to any one of aspects 14 to 20, wherein the temperature control, system is adapted to create a temperature rise in the sample probe lying in the range from about 0° C. to 100° C. preferably from 2° C. to 50° C. and more preferably from 5° C. to 20° C.

22. Device according to any one of aspects 14 to 21, wherein the device is adapted to receive a sample probe having a volume lying in the range from, about 1 μl to 100 μl, preferably from 0.1 μl to 30 μl and also preferably from 0.5 μl to 5 μl.

23. Device according to any one of aspects 14 to 22, wherein control means is adapted to control the time span between the first time and the second time to lie in the range from about 1 μs to 60 min, preferably about 0.01 see to 20 min, preferably about 1 sec to 10 min, preferably 60 sec to 5 min.

24. Device according to any one of aspects 14 to 23, wherein the detection means is adapted to conduct the detection at the surface, the bottom, the side of the measurement chamber or the sample probe and/or at a predetermined distance from heating means or at a place of specific temperature, preferably close to the heating means or near a surface in a region of high temperature gradients 25. Device according to any one of aspects 14 to 24, wherein the device is adapted to measure a plurality of sample probes subsequently and/or in parallel.

26. Device according to any one of aspects 14 to 25, wherein the device comprises a substrate containing a measurement chamber for receiving the sample probe.

27. Device according to any one of aspects 14 to 26, wherein the measurement chamber and/or the sample probe is covered by a cover lid.

28. Device according to claim 27, wherein the cover lid comprises one or more filling holes and/or pin holes.

29. Device according to any one of aspects 14 to 27, wherein the measurement chamber is defined as a recess in the substrate.

30. Device according to any one of aspects 14 to 29, comprising filling holes for filling the measurement chamber, 31. Device according to any one of aspects 14 to 30, wherein one or more of the heating and/or cooling means of the temperature control system extend into and/or through the measurement chamber and/or the sample probe, 32. Device according to any one of aspects 14 to 31, wherein one or more of the heating and/or cooling means of the temperature control system contacts the measurement chamber and/or the sample probe.

33. Device according to any one of aspects 14 to 32, wherein one or more of the heating and/or cooling means are electrically isolated vis-à-vis the measurement chamber and/or the sample probe, preferably by an electrical isolation coating and/or an electrical isolation layer.

34. Device according to any one of aspects 14 to 33, wherein the measurement chamber and/or the sample probe is covered by a cover lid and wherein the cover lid is a heating and/or cooling element, preferably an TTO element, 35. Device according to any one of aspects 14 to 34, wherein the measurement chamber is defined by a structured surface and/or the sample probe is a positioned on a surface of a substrate as a droplet and where the heating and/or cooling element is defined by/on/in the substrate on which the droplet is placed.

36. Device according to any one of aspects 14 to 35, or method according to any one of aspects 1 to 13, wherein the temperature of the measurement chamber and/or the sample probe can be/is controlled in a way that biochemical reactions such as PCR can be carried out 37. Method to measure thermo-optical, particularly thermophoretic, characteristics of particles in a solution by using a device according to any one of aspects 14 to 36.
38. Use of any of the methods according to aspects 1 to 13 or 37 or any of the devices according, to aspects 14 to 36 for the characterization of thermo-optical, particularly thermophoretic properties of particles in solution.
39. Use of any of the methods according to aspects 1 to 13 or 37 or any of the devices according to aspects 14 to 36 for the determination of surface properties of particles in solution.
40. Use of any of the methods according to aspects 1 to 13 or 37 or any of the devices according to aspects 14 to 36 for the separation of particles in solution according to the thermophoretic properties of said particles.
41. Use of any of the methods according to aspects 1 to 13 or 37 or any of the devices according to aspects 14 to 36 for the characterization of interactions of biomolecules in solution.

According to a first embodiment of the present invention, the elements of the temperature control system preferably have in common that their heating/cooling-elements/devices use electric current to generate a localized thermal distribution, e.g. a localized temperature gradient. The approaches used for generating the temperature profile or gradient by means of electric current can be distinguished into two different types of conducting the electric current. Direct conducting and capacitive conducting. The preferred embodiments described in the following use preferably structures of heating elements in the micrometer range. Such structures can be fabricated easily using standard, lithography techniques, but if more locally defined temperature gradients are preferred it is possible to achieve submicron resolution using high-end techniques, e.g. electron beam lithography.

These heating elements may be combined with various embodiments of measurement chambers to hold a sample probe and provide a defined volume for the detection, it is preferred that the heating element(s) are in contact with the measurement chamber to dissipate the generated temperature via thermal conduction, to the solution with the marked particles to be measured, if the detection method by its nature is constrained to a given, and reproducible area of the sample e.g. TIRF or electrical detection, there is no need for any other confinement of the test fluid and thus the analysis could even be performed using a droplet on top of the heating structure.

Thus, according to a preferred embodiment no structurally predefined measurement chamber is needed. However, in line with the general understanding of the person skilled in the art, also functionally defined measurement chambers, e.g. as referred to above, are included to be encompassed by the term measurement chamber. Such functionally defined measurement chambers include, e.g., a droplet on a substrate which may be covered by a lid.

Some devices according to the present invention may comprise an additional cooling element/device to improve the created temperature gradient. All geometries of the measurement chamber discussed later in the detailed description can be combined with all presented approaches to generate a local temperature distribution and induce thermophoresis that are described herein.

As discussed before, a current flow through an ohmic conductor results in heat generation inside the conducting material, an effect known as Ohmic or Joule heating. This effect is used in the invention to create a locally defined temperature distribution/gradient in the sample probe which leads to a thermophoretic motion.

In order to generate a highly localized temperature gradient a conducting material, e.g. a heating wire, is preferably arranged on an appropriate support substrate, e.g. glass, silicon, or polystyrene. Such a heating wire is preferably arranged with an electrically isolating (siliciondioxide) layer between the conducting material and the sample probe in order to avoid any undesired chemical reactions between the solution of the sample probe and the heating element. As conduction material gold may be advantageously used since it is easy to handle and process. But the effect of heat generation is not restricted to gold and works with any conductive material. The term "wire" or "wires" relates in the context of this invention and in particular in the claims, to normal wire but also to continuous structures made of conductive material which is brought on a given substance. In particular, gold structures vaporized on a substrate are used as "wires" in some embodiments. In some embodiments this heating is obtained using, an insulated heating wire, preferably 10 μm to 1000 μm thick and/or wide and/or in diameter.

The heat is conducted into the sample and results in a temperature profile in the chamber. This steady-state profile is reached after waiting about some seconds to some minutes. The temperature decays logarithmically with the radial distance from the wire. The shape of the decay does not change with the thickness of the wire or the used material. An preferred additional thin electrical isolating layer around the heating wire does typically not disturb the temperature distribution in the fluid.

It is further preferred that the temperature profile is quite narrow. The dimensions of the heating elements, e.g., the heating wire, are preferably small. According to a preferred example, a wire may be 5 micron wide and 50 nm in height. The resistance of an ohmic conductor is $R=r*1/A$, the power generated in the conductor is $P=R\ I^2$. In case the power dissipated in the heating area should be maximized, the wires towards the heating region are preferably much wider than in the hearing region itself. In the example these wires have a width, of microns. This layout is also applicable in microchannels or capillaries.

In microchannels the heating structure or heating wire may be added during the fabrication process and brought on the bottom, the top or the side walks) of the channel/microchannel. In case the measurement chamber is provided as a capillary, the heating elements or the heating wire is preferably brought onto the outside of the capillary. This can be done both along the axis of the capillary or perpendicular to said axis.

In particular, the heating element (e.g. a heating wire) may be added onto an outer wall of a capillary what exhibits a direct contact of the sample solution inside the capillary and thus unwanted electrode reactions. Some embodiments may comprise heating elements in form of electrodes at opposite sides of the capillary. The shape and the size of the electrodes determine the size of the heating spot. Other embodiments may comprise two ring electrodes around the capillary with a given gap distance between the two electrodes. The heat distribution is created in between the electrodes.

To avoid reactions of the metal structure with the sample probe and the solution, an additional or alternative and preferably very thin $SiO_2$ layer may be provided over the structures. In particular, a very thin $SiO_2$ layer does not disturb the temperature gradient bat inhibits any unwanted chemical reactions.

Due to the preferred small distances used in the measurement structure high electric fields and large power densities are generated in the sample probe next to the heating elements/structures. The temperature rise $$\Delta T = \left| \frac{\sigma V_{rms}^2}{8k} \right|$$

for σ=0.1 S/m and V=10V peak to peak applied over the electrolyte between the two structures and k=0.6 J/(m s K) is ΔT=1K. Thus, higher voltages or high conductive solutions with σ>0.1 are preferred to achieve sufficient high temperature rises because it is preferred to keep the salt, concentration low as the Soret coefficient decreases with an increase in salt.

A preferred advantage of the heating technique described above is the creation of temperature distributions more localized than it is possible with standard microscopy optics and IR-Lasers since structures in the submicron regime can be created. The contact beating according to the present invention further avoids expensive focusing optics as required by IR-Laser radiation heating, because it is not necessary to focus the IR-beam to absorb the laser power in the absorbing material. Moreover, as generally in line with the present invention, any solution, e.g., polar solution, non-polar solution, organic solution or aqueous solution, may be used as well as any combination of those. Moreover, the heating technique describe above allows an efficient and easy defined parallelisation of measurement chambers with sample-probes to be heated, in particular also in view of the known methods to control such heating.

According to another aspect of the present invention, the heating/cooling structure may be provided macroscopically instead of providing micro-structured heating elements. For instance, a measurement chamber with a heated top plate may be provided, wherein substantially the entire top plate is heated by a heating element/device. Additionally or alternatively the bottom, preferably a substantial part of the bottom of the measurement chamber may be cooled with a cooling element/device. Such a macroscopic arrangement provides the advantage to maintain a constant temperature profile (gradient) inside the chamber, preferably in one direction, preferably in the z-direction (direction of gravity if upper and lower is defined with regard to gravity). Such a chamber may be made of a glass slide, a glass cover slip and a spacer foil including a cut-out for the sample.

In particular, a measurement chamber according to this aspect typically comprises two or three main parts, namely a base or bottom plate or substrate, preferably optional confinements at the sides, and a cap or cover. All of these preferably comprise special material properties. The base plate or substrate and the cap are preferably made of material of high thermal conductivity but still be inert to the sample, e.g. the biomolecules, in the chamber. A cap or cover lid may close the measurement chamber and may further reduce or avoid vaporisation of the sample probe or solution during the measurement. According to a preferred embodiment of the present invention, the cap of the chamber and/or the substrate is transparent to allow an optical detection from above and/or below. For instance, the cap may be made of sapphire only some hundreds of micron in height. For the chamber's base plate silicon may be used. This material provides a high thermal conductivity and it is easy to add an inert layer on top of the base plate, e.g. silicondioxid. In principle this base plate can be of any high conductive material like e.g. metals with an inert interface to the chamber e.g. by an additional very thin glass layer.

If the steepness of the temperature gradient is not crucial, for the measurement it is possible to use glass for the cap and/or the base plate instead of the sapphire and silicon to reduce the production costs of the chamber.

The heating element may be a metal plate attached to the cap of the measurement chamber and/or may comprise heating foils attached to a metal contact plate. For an observation of the analysis inside the chamber the metal and/or the contact plate preferably comprises an observation window directly above the chamber.

Another type of heating element may comprise a thin layer of indium tin oxide (ITO) vaporized on the cap of the measurement chamber. ITOs main feature is the combination of electrical conductivity and optical transparency. This ITO layer allows heating the cap of the measurement chamber directly and still observing the signal inside the chamber from above.

The cooling element may comprise a metal contact plate and a Peltier element which electrically generates the cooling of the chambers base plate. Alternatively, e.g. a water cooling can be used to cool the contact plate and/or the base plate of the chamber.

The temperature of the cap and bottom of the measurement chamber is preferably measured using temperature sensors attached to the outer faces of the measurement chamber. These allow the determination of the temperature gradient inside the measurement chamber when a high thermal conductive material is used for the cap and base plate. Otherwise the temperature detected on the outer faces is higher than at the inner faces as a given amount of heat drops inside the cap and base plate. To get the correct temperature and temperature gradient the measurement temperature value have to be corrected for the drop.

The optional confinements of the measurement chamber are preferably made of material which is inert to the biomolecules and does not show high thermal conductivity. This is the case for Biaxially-oriented polyethylene terephthalate (boPET) polyester Elm (Mylar foil) or Polydimethylsiloxane (PDMS) layers. These foils are available at accurately defined heights to exactly define the height of the measurement chamber. A higher thermal conductivity of the confinement generates a higher heat flow through the chamber and thus more power is necessary to maintain the thermal gradient over the chamber.

According to a preferred embodiment, the temperature gradient is applied vertically, heating the upper border of the chamber and cooling the bottom. The orientation of the temperature gradient is preferred in this direction to avoid the effect of Rayleigh-Benard convection of the fluid. In particular, when heating the chamber from, below the liquid at the bottom becomes less dense and moves away from the lower surface driven by buoyancy forces. At the top, the liquid cools again, thus moves back to the bottom and convection cells are formed.

Concerning the measurement time the height of the measurement chamber is a crucial factor. Higher chambers result in longer duration for the measurement. Thus, chamber heights between 1 to 3000 microns are preferably used, depending on the desired speed of the measurement and the detection, method in use.

The heating/cooling elements described above can be combined with various detection types. For instance, the thermophoresis signal can be detected using epifluorescence microscopy combined with a narrow z-focus of the objective. TIRF microscopy, confocal microscopy or any other detection method which does preferably not integrate the fluorescence over the whole chamber but allows a discrimination of the fluorescence through the chamber in z-direction.

Preferably, the detection of the thermophoresis signal is performed optically using fluorescent dyes attached to the panicles of interest. Therefore the fluorescence intensity is preferably measured from above using a light detecting device, e.g. a CCD camera or a photomultiplier. Any light detecting device with spatial resolution allows using statistics to improve the signal, as every pixel recorded contains the complete information about the particles. In this way the change in the concentration in every spot of the temperature distribution can be observed. From the intensity profile of the fluorescent dyes the concentration profile can be calculated taking into account the profile of the concentration as well as the fluorescence of the bulk above the heated region which only contributes to the background. Thus height of the measurement chamber has to be known and further highly reproducible to compare different measurement or the height is measured using the intensity of a standard, reference which can be an additional fluorescence dye err the fluorescence label of the particles but observed in a region which is not affected by the heating. This height can be used in the calculation of the concentration profile and correct against this bulk background.

To avoid this correction, some embodiments use a TIRF illumination (Total internal Reflection Fluorescence) which only excites fluorescence about 100 nm above the surface. This reduces the fluorescent background signal of the bulk fluid above the heat regime.

Other embodiments relate to a limited depth of field (DOF). In particular, such embodiments may use a pinhole which limits the spatial z-focus of the objective used for observing the thermophoresis signal. In some embodiments a confocal microscope is used.

The embodiments using this illumination and/or detection methods also do not need any measurement chamber but can measure the signal for example in a droplet. In other words, these methods do not need the information of the height of a measurement chamber such that a droplet or a chamber with a unknown height may be used.

The detected change in concentration is related to the known temperature profile. This temperature profile is measured once using temperature sensitive fluorescent dyes, e.g. BCBCF in TRIS buffer, Cy5 other. The temperature profile stays unchanged for unchanged environment conditions. For higher confidence the temperature profile can be measured in parallel using an additional fluorescent dye in the sample fluid.

With, the detection device not only the thermophoretic movement may be measured but also the back diffusion of the depleted particles when the heating element is switched off. This back diffusion provides information about the diffusion coefficient of the sample.

Without differing from the gist of the invention it is also envisaged that instead of detection based on fluorescence other detection methods are possible. Depending on the size and properties of the particles to be detected, the step of fluorescently exciting may be omitted, and detection based on light scattering, Rayleigh Scattering, (UY) absorption, phase contrast, phosphorescence and/or polarisation are possible. Moreover, for particles larger than 100 nm, the movement of such particles can be detected by single particle tracking.

In some embodiments the detection of thermophoresis are implemented in an electrical manner. For detecting thermophoresis electrically, a current signal through the sample is observed which changes its signal strength due to the heating of the chamber and the thermophoretic motion of the charge carriers and probe molecules. The great advantage of such a measurement scheme is that it works without labelling or marking the sample's particle and that no difficult measurement setup is necessary, in the current signal the movement of the particles and their steady state is then detected.

Like larger particles, also ions show a thermophoretic motion in a temperature gradient. Thus the conductivity alters when the ions move due to the created temperature gradient. But as ions are much smaller than the observed particle their diffusion occurs on shorter time scales and thus does not interfere with the thermophoresis signal of DNA or other larger particles.

The detection preferably uses an AC-current which is applied over probe electrodes. Any change in the dielectric may be recognized, movements of charged particles as well as changes of uncharged but polarizable particles.

In contrast to the capacitive-electric detection used for capillary electrophoresis no peak detection is performed but quantitative concentration detection. The detection scheme for capillary electrophoresis uses the detection signal and combines it with an external measured flowing time. The electric detection used for thermophoresis uses a quantitative determination of the concentration and combines it with the knowledge about the temperature in the measured spot. This provides information about the particles' properties without any solid phase and external pumping system.

A preferable embodiment for such an electric detection uses probe electrodes which are added near the heated area. For a structure using a heating, wire the probe electrodes are preferably added to the substrate using the same technique as for adding the heating wire. The probe electrode allows detecting the movement of particles in the r-direction (radial direction).

Using the information about the steady state concentration at a given spot and the spot's temperature the Soret coefficient $S_T=D_T/D$ may be calculated. This coefficient is highly sensitive on change of size or surface properties. A small change of the particle's surface-caused by interaction with other particles e.g. proteins or antigens result in a strong signal in the thermophoresis signal.

The Soret coefficient also provides information about the size of the particle but for a determination of the hydrodynamic radius it is more convenient to use the diffusion coefficient alone.

The sensitivity allows the detection of binding of particles with identical surface properties and the formation of crystals made of these particles.

BRIEF DESCRIPTION OF THE DRAWINGS

The invention will now be described in detail with respect to preferred embodiments with reference to accompanying drawings, wherein:

FIGS. 3a-e show a measurement chamber with a wire perpendicular to the measurement chamber as heating element in a top view and a cross-sectional front view.

FIGS. 6a-c show three preferred heating structures according to the present invention in a top view.

FIG. 6d shows an array of heating structures as shown in FIG. 6a.

FIGS. 7a-e show different measurement chambers according to the present invention with heating structures similar to FIG. 6a.

FIGS. 5a-b show electrical field heating structures according to the present invention in an enlarged top view.

DETAILED DESCRIPTION OF THE INVENTION

The present invention provides methods and devices for the analysis of particles in samples dissolved in liquids using thermophoresis.

Figure 1:
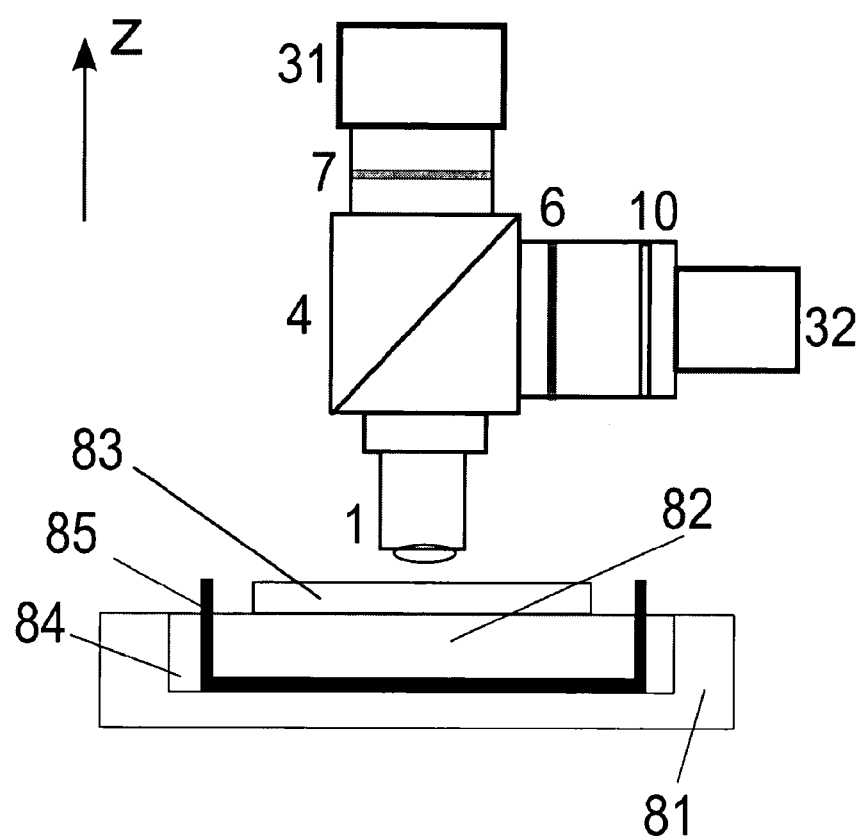
FIG. 1 show an fluorescence microscope according to the present invention.

FIG. 1 shows an example of a microscope (e.g. scanning microscope, fluorescence microscope, confocal microscope) according to the present invention. The device comprises in the upper part a means for detection or a detection system for detecting, measuring and/or exciting the marked particles and in the lower part a measurement chamber with a preferred temperature control system for generating a spatial temperature distribution/gradient.

In the following different embodiments of the detection, and/or exciting means will be discussed in detail which may be combined with any kind of measurement chamber and/or temperature control systems as discussed above and below.

The detection system is preferably based on a standard fluorescence microscopy setup. In particular, the detection system comprises a optical system for exciting, preferably luminescently exciting, more preferably fluorescently exciting the marked particles provided in a sample probe located in the measurement chamber 82 with light from a light source or excitation source 32, e.g. a Laser. Fibre Laser. Diode-Laser, LED, FfXF, Halogen, LED-Array, HBO.

The light for excitation and the emitted light from the excited particles may be focussed with an optical lens system 1 which comprises one or more lenses. The optical lens system 1 is preferably an objective 1. e.g. 40×, NA 1.3, oil immersion, ZEISS "Fluar".

A dichroic mirror/beam splitter 4, preferably, reflecting short wavelength (R>80%) and transmitting long wavelength (T>80%) is arranged above the objective 1 and adapted to guide (reflect) light from the excitation source 32 through the objective to the measurement, chamber 82 (horizontal or excitation arm). Furthermore, the beam splitter allows passing the light from the excited panicles to pass though the beam splitter to a detector 31 arranged above the beam splitter 4 (vertical or detection arm). An excitation filter 6 (e.g. band pass/long pass) and/or a lens system 10 to determine the beam properties of the excitation light source 32 may be further arranged between the beam splitter 4 and the excitation source 32. The lens system 10 may comprise one, two or more lenses. An emission filter (band pass/long pass) 7 is preferably arranged between the beam splitter 4 and the detector 31, which may be a CCD-Camera, Line-Camera, Photomultiplier Tube (PMT). Avalanche Photodiode (APD), CMOS-Camera.

The system may alternatively and/or additionally comprise other components as would ordinarily be found, in fluorescence and wide field microscopes. Examples for means of excitation and detection of fluorescence may be found in: Lakowicz, J, R. Principles, of Fluorescence Spectroscopy, Kluwet Academic/Plenum Publishers (1999).

The measurement chamber 82 containing the sample probe (e.g. the sample probe comprising marked particles in a solution), comprises at least an optical transparent site such that fire excitation by means of light and the optical detection of the particle properties is possible. The measurement chamber 82 as shown in FIG. 1 comprises an optical transparent cover lid 83 at the upper site. The detections system is preferably placed at an optical transparent site or place of the measurement chamber 82, e.g. the detections system is placed on the upper side of fee measurement chamber 82 next to the transparent lid 83.

The measurement chamber 82 is preferably temperature controlled by means of a temperature control system in order to create the desired temperature distribution and/or temperature gradient within the sample probe located in the measurement chamber 82. The measurement chamber 82 is preferably arranged, on a substrate 81 to mechanically support the measurement chamber. The measurement chamber preferably comprises a cover lid 83 on the top. A heating element 85, here in form of a wire is arranged, such that the sample probe in the measurement chamber 82 can be heated via contact heating, i.e. the heating energy provided by the heating element 85 is conducted to the sample probe located in the measurement chamber 82. The substrate 81 comprises preferably a defined heat conductivity, and may be made of glass, silicon with an isolating layer, sapphire, diamond, PDMS (Polydimethylsiloxane), plastic, synthetic material, ceramics, metal-ceramic mixture, glass based composite, and/or composite material. The cover lid 83 is preferably optical transparent, preferably thin, and may be made of glass, sapphire, diamond, synthetic material and/or plastic. The heating element 85 for generating the temperature distribution/gradient is preferably a thin wire, preferably surrounded by a thin electrical isolating layer 84 (e.g. silicon dioxide). Additionally or alternatively, the heating element may be embedded in an electrical isolating layer 84 covering the bottom surface or a part of the bottom surface of the measurement chamber. The electrical isolating material is preferably inert to the sample probe. The wire may be a wire of copper, gold, silver, platinum, wolfram, or other metals.

Moreover, the measurement chamber 82 has preferably a defined height and preferably a defined volume. Preferably the measurement chamber is oriented in a defined angle to the direction of gravitation, more preferably the chamber is oriented to the direction of gravitation in such away, that thermal convection is minimized.

Figure 2:
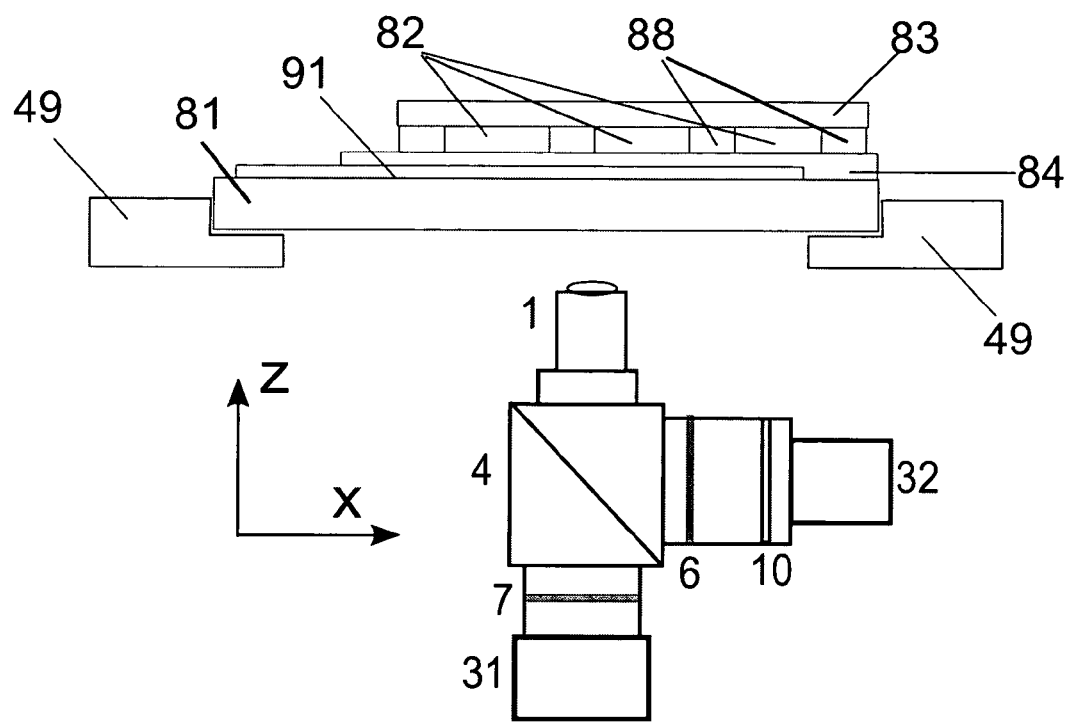
FIG. 2 shows another embodiment of a microscope according to the invention.

FIG. 2 shows a further embodiment according to the present invention similar to the embodiments shown in FIG. 1. However the embodiment preferably comprises more than one sample containing measurement chamber 82, separated by spacers 88. Moreover, the spacers 88 have preferably a defined height (e.g. 50 µm, 500 µm, 250 µm, 500 µm) and the material of the spacers is preferably chemical inert (e.g. PDMS, Teflon), preferably it is inert to the solution containing the marked particles. Each measurement chamber is preferably in direct thermal contact with the heating structure 91. Moreover, the heating structure 91 is preferably a thin layer of a preferably conductive material (e.g. gold, silver, platinum, ITO) and is preferably optical transparent (e.g. ITO). The heating structure is preferably surrounded by a thin electrical isolating layer 84 and is preferably placed onto the substrate 81. The electrical isolating layer 84, preferably a nanometer thick layer of silicon dioxide, preferably prevents the direct contact between the solution in the measurement chambers 82 and the electrical conductive heating structure 91. The substrate 81 may be placed on a translation stage 49, preferably a xy-translation stage, for moving the measurement chamber preferably relative to the detection system. Also the detection system may be movable, preferably with a translation stage, maybe a xyz-translation stage, a xy-translation stage, a xz-translation stage, a yz-translation stage, a x-translation stage, a y-translation stage or a z-translation stage.

The detections system is preferably placed at an optical, transparent site or place of the measurement chamber 82. e.g. the detections system is placed on the lower side of the measurement chamber 82 next to the transparent substrate 81 and the preferably transparent heating structure 91. The detection system may also be placed on the upper side of the measurement chamber 82 next to a preferably transparent cover lid 83.

Figure 3A:
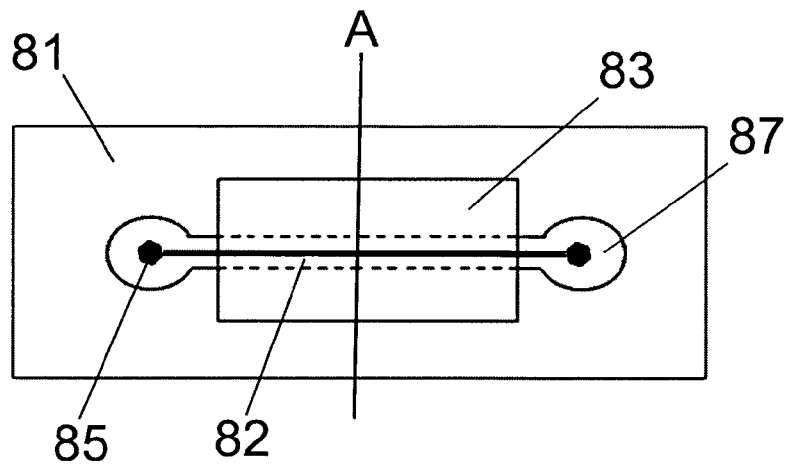
FIGS. 3a-c show a measurement chamber with a wire along the measurement chamber as heating element in a top view, a cross-sectional side view and a cross-sectional front view.

FIG. 3a shows a further embodiment according to the present invention similar to the embodiments shown in FIG. 1. However the filling holes 87 for filling the measurement chamber 82 with a solution of marked particles may be placed inside the substrate 81 on two opposite sides of the cover lid 83. Preferably the elongated side of the measurement chamber 82 may be oriented parallel with respect to the heating element 85 (e.g. a wire). Preferably the measurement chamber 82 may have a defined volume, preferably in the range of 1 µl to 200 µl.

Figure 3B:
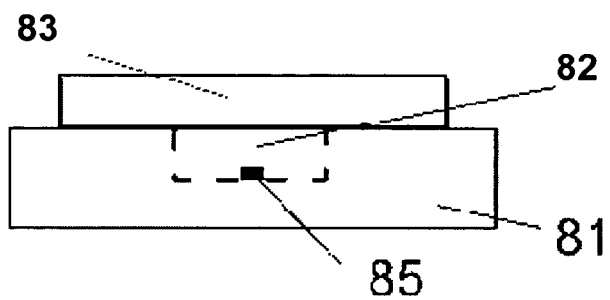

FIG. 3b shows a cross section along line A of the embodiment shown in FIG. 3a. Preferably the measurement chamber 82 is formed by the preferably temperature, controlled substrate 81 and covered by a preferably transparent cover lid 83. Preferably the heating structure 85 (e.g. a thin wire) is placed in the middle of the bottom of the measurement chamber 82.

Figure 3C:
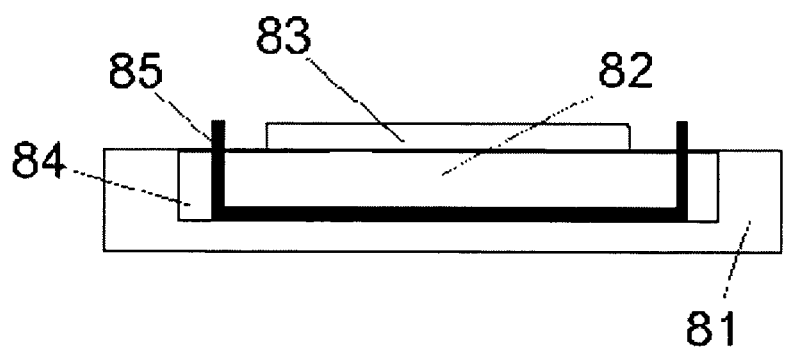

FIG. 3c shows a further embodiment according to the present invention similar to the embodiments shown in FIG. 1. However the measurement chamber 82 containing the solution with the particles is shown without detection system. Preferably this embodiment is used for the inducing of the thermophoretic movement of particle's, without a simultaneous detection of said particle's. The measurement, of the marked particles inside the measurement chamber 82 may be done by optical systems like laser scanning systems, by systems and devices using absorbance measurements, by systems and devices measuring the scattering of light, by systems and devices measuring the polarization of light and/or by systems measuring radioactivity.

Figure 3D:
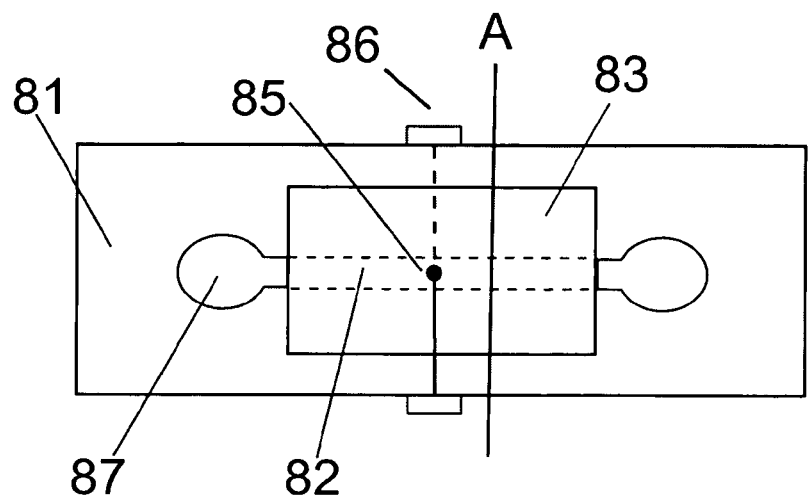

FIG. 3d shows a further embodiment according to the present invention similar to the embodiments shown in FIG. 1 and FIG. 3a. However the heating structure 85 (e.g. a wire) is oriented perpendicular with respect to the cover lid 83 and the elongated side of the measurement, chamber 82. The contact pads 80, preferably with electrical contact to the heating structure 85, may be of the same material as the hearing structure 85. The contact pads 86 are preferably used to connect the heating structure 85 to a means of electrical power/current (e.g. a power supply, DC power supply. AC power supply). The contact pads 86 may be placed at different sides of the substrate 81. Preferably the contact pads 86 are isolated electrically from the substrate 81.

Figure 3E:
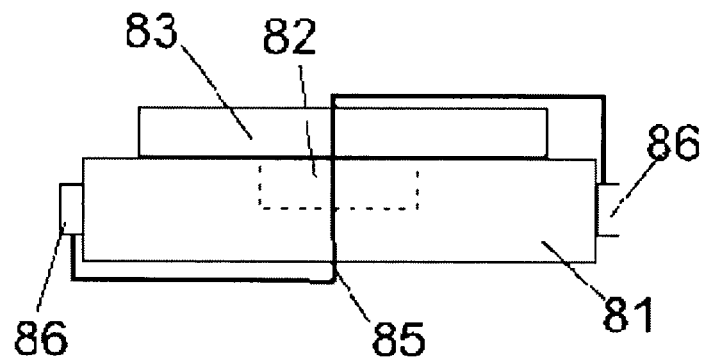

FIG. 3e shows a cross section of the embodiment shown in FIG. 3d along line A.

Figure 3F:
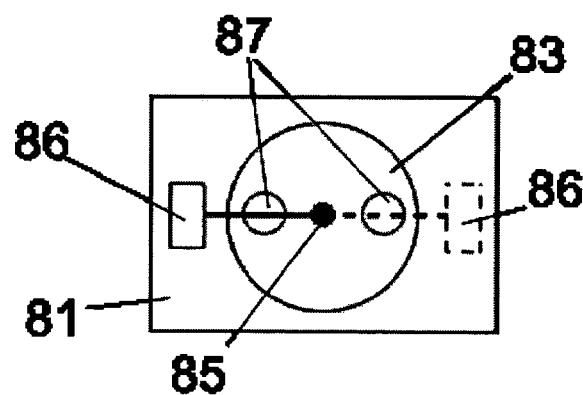
FIGS. 3f-g show a measurement chamber with a wire perpendicular to the measurement chamber as heating element in a top view and a cross-sectional front view similar to the embodiment as shown in FIGS. 3d and 3e.

FIG. 3f shows a further embodiment according to the present invention similar to the embodiments shown, in FIG. 3d. However the contact pads 86 may be placed at the top and/or the bottom of the substrate 81 and the filling holes 87 may be located at the cover lid 83.

Figure 3G:
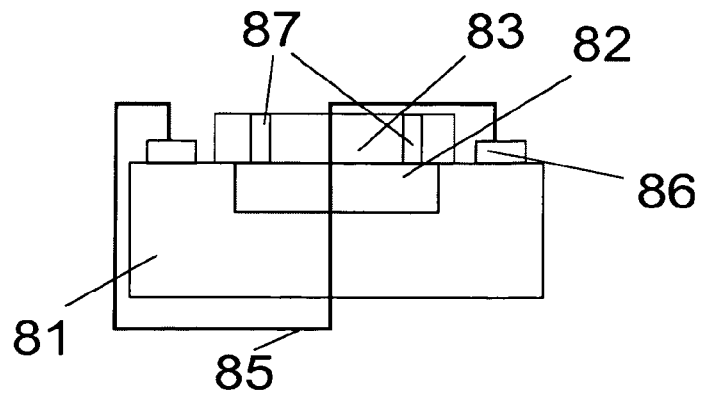

FIG. 3g shows a cross section of an embodiment similar to the embodiment shown in FIG. 3f. However the contact pads 86 may be placed at one side of the substrate, preferably the top of the substrate.

Figure 4A:
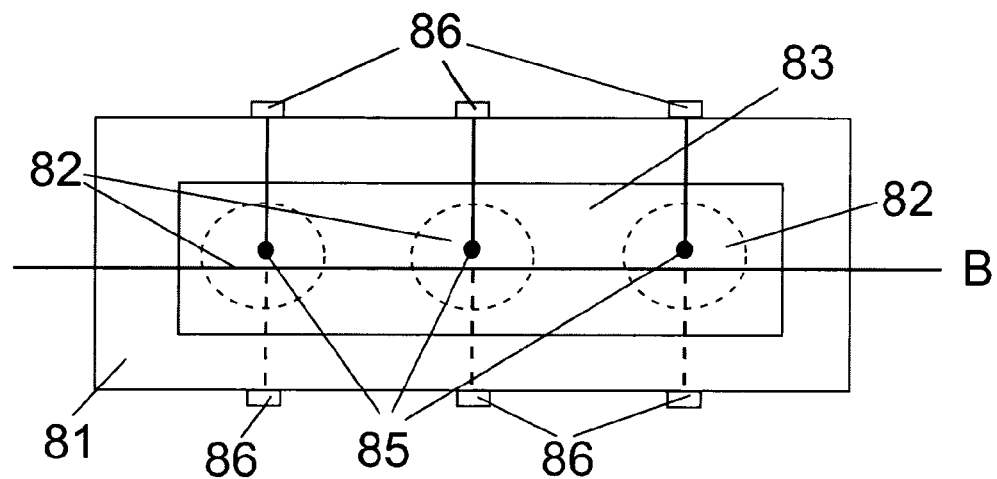
FIGS. 4a-b show an array of three measurement chambers, each chamber with a wire perpendicular to the measurement chamber as heating element in a top view and a cross-sectional front view.

FIG. 4a shows a further embodiment according to the present invention similar to the embodiments shown in FIG. 3d and FIG. 3e. However in this embodiment more than one measurement chamber 82 is placed between substrate 81 and cover lid 83. The measurement chambers 82 are preferably separated by walls formed by the substrate 81. Preferably the measurement chambers 82 have a defined geometry in the plane of the substrate (e.g. circle, square, rectangle). The chamber may contain a heating structure 85 (e.g. a wire) and each heating structure may be contacted via two contact pads 86. Each heating structure 85 is preferably individual addressable by means of electrical contact and/or electrical circuit design. The heating structures 85 in different measurement chambers 82 may be controlled to generate different temperature distributions in different measurement chambers 82 or to generate preferably identical temperature distributions in different measurement chambers 82.

Figure 4B:
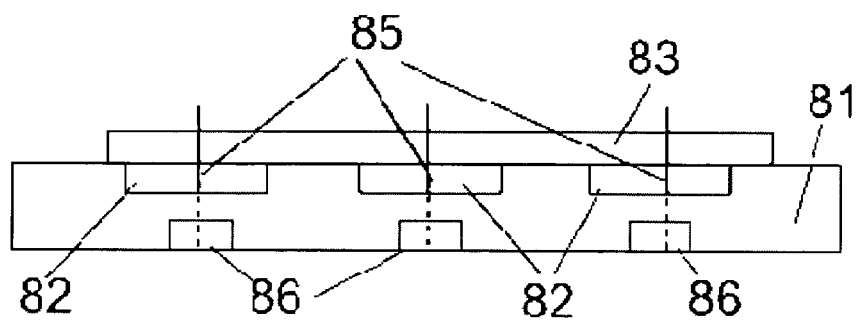

FIG. 4b shows across section of the embodiment shown in FIG. 4a along line B.

Figure 5A:
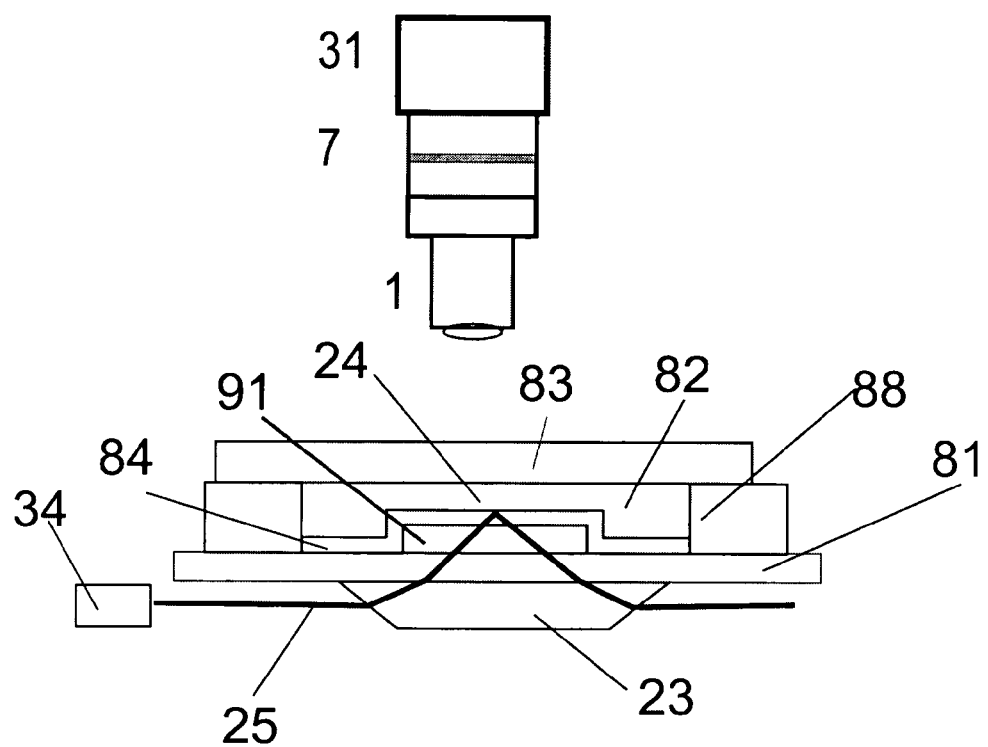
FIG. 5a show a further embodiment of the present invention with a detection system based on a microscopy setup for the measurement of TIRF.

FIG. 5a illustrates a particular embodiment of a device accordingly to the present invention, in particular a setup for generating, a spatial temperature distribution and for measuring the thermophoresis of marked panicles. The detection system, may be based on a standard microscopy setup for the measurement of TIRF (total internal reflection, fluorescence). The marked particles are preferably excited by means of an evanescent wave and the fluorescence of said particle is preferably detected by a means of defection, preferably a microscopy setup containing emission filters. The evanescent wave for the preferably local excitation of the fluorescence, preferably in a distance within preferably 150 nm from the surface of the isolation layer 84 at the heating structure 91 on the substrate 81, is preferably generated at a defined place 24. The TIRF excitation may comprise a light/excitation source 34 and a prism 23. The light/excitation source 34, may be a laser, a fibre coupled laser or a LED. The excitation source may also comprise optical elements like lens systems, preferably to provide beam characteristics sufficient for TIRF. The light beam 25 is preferably directed to the interface between the solution of marked particles in the measurement chamber 82 and the isolating layer 84 by a prism 23 (e.g. a dove prism). Preferably an index of refraction matching oil is placed between prism 23 and substrate 81. Preferably the prism 23 is temperature controlled. Preferably at the place 24 the marked particles are excited fluorescently by the generated evanescent wave, allowing for the measurement of TIRF. The fluorescence of said excited particles is preferably detected with a microscope setup comprising an optical lens system 1 which comprises one or more lenses. The optical lens system 1 is preferably an objective L e.g. 40×. NA 1.3, oil immersion, ZEISS "Fluar" and an emission filter (band pass/long pass) 7 is preferably arranged between the optical lens system 1 and the detector 31, which may be a CCD-Camera. Line-Camera, Photomultiplier Tube (PUT), Avalanche Photodiode (APD), CMOS-Camera, SPM (silicon multiplier tube).

The measurement, chamber 32, containing the solution of the marked particles, is preferably temperature controlled and has preferably a defined height and preferably a defined volume. Preferably the measurement chamber is oriented in a defined angle to the direction of gravitation, more preferably the chamber is oriented to the direction of gravitation in such a way, that thermal convection is minimized. In detail the measurement chamber is placed on or in a substrate 81, preferably an optical transparent substrate, and is covered with a cover lid 83, preferably an optical transparent cover lid, and comprises a heating structure 91. Furthermore the cover lid is preferably optical transparent, preferably thin and maybe glass, sapphire, diamond, synthetic material, plastic. Moreover the cover lid 83 may also be temperature controlled. The substrate 81 preferably has a defined heat conductivity and may be glass, silicon with an isolating layer, sapphire, diamond, PDMS (Polydimethylsiloxane), plastic, synthetic material, ceramics, metal-ceramic mixture, glass based composite, composite material. The Isolating layer 84, may be silicon dioxide, preferably the thickness of the layer is only a few nanometers and preferably the isolation layer is optical transparent. The thickness of the measurement chamber 82 may be defined by a spacer 88, may be PDMS, silicon rubber, plastic, synthetic material. The measurement chamber preferably comprises a preferably transparent heating structure 91, may be a microstructure with a small thickness, (e.g. 100 nm, 1 μm, 10 μm), preferably forming a pattern in the plane parallel to the surface of the substrate 81. The material of the heating structure 91 may be gold, platinum, silver, ITO.

Figure 5B:
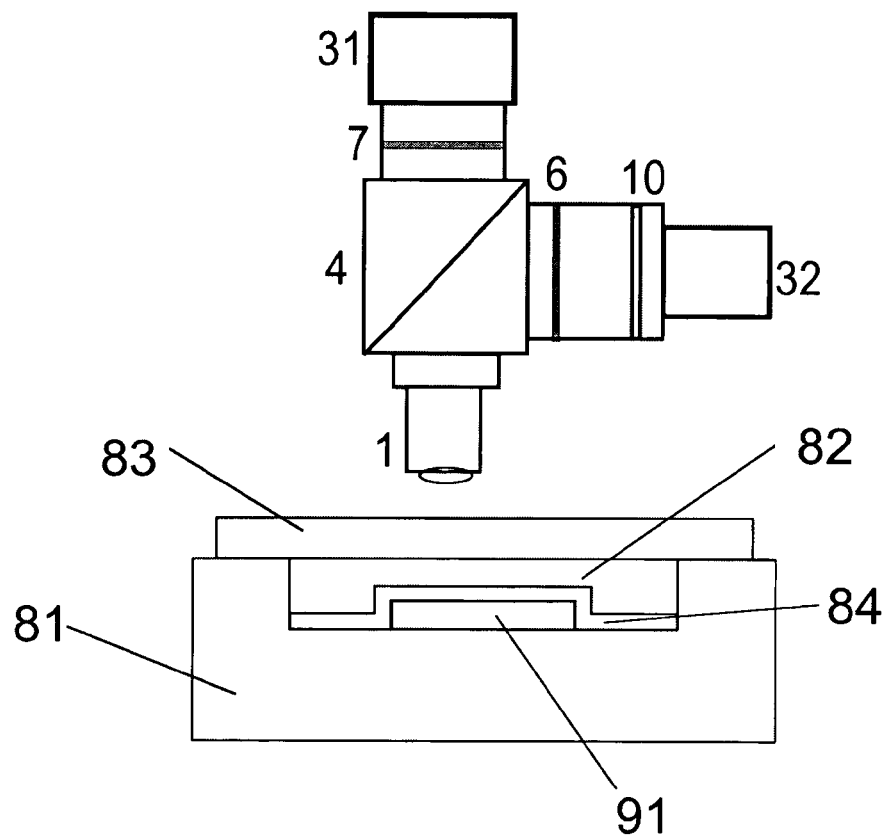
FIG. 5b show a further embodiment of the present invention with a detection system similar to FIG. 1 but wife a heating structure.

FIG. 5b shows an example of a microscope (e.g. scanning microscope, fluorescence, microscope, confocal microscope) according to the present invention. The device comprises in the upper part a means for detection or a detection system for detecting, measuring and/or exciting the marked particles and in the lower pan a measurement chamber with a preferred temperature control system, for generating a spatial temperature distribution/gradient. Here, it is to be noted that generally in line with the present invention the detection means and the excitation means may preferably be provided as one multifunctional device.

In the following different embodiments of the detection, and/or exciting means will be discussed in detail which may be combined with any kind of measurement chamber and/or temperature control systems as discussed above and/or below.

The detection system is preferably based on a standard fluorescence microscopy setup. In particular, the detection system comprises a optical system for exciting, preferably luminescently exciting, more preferably fluorescently exciting the marked particles provided in a sample probe located in the measurement chamber 82 with light from a light source or excitation source 22, e.g. a Laser, Fibre Laser, Diode-Laser, LED, HXP. Halogen, LED-Array, HBO.

The light for excitation and the emitted light from the excited particles may be focussed with an optical lens system 1 which comprises one or more lenses. The optical lens system 1 is preferably an objective 1, e.g. 40×, NA 1.3, oil immersion, ZEISS "Fluar".

A dichroic mirror/beam splitter 4, preferably, reflecting short wavelength (R>80%) and transmitting long wavelength (T>80%) is arranged above the objective 1 and adapted to guide (reflect) light from the excitation source 32 through the objective to the measurement chamber 82 (horizontal or excitation arm). Furthermore, the beam splitter allows passing the light from the excited particles to pass though the beam splitter to a detector 31 arranged above the beam splitter 4 (vertical of detection arm). An excitation filter 6 (e.g. band pass/long pass) and/or a lens system 10 to determine the beam properties of the excitation light source 32 may be further arranged, between, the beam splitter 4 and the excitation source 32. The lens system 10 may comprise one, two or more lenses. An emission filter (band pass/long pass) 7 is preferably arranged between the beam splitter 4 and the detector 31, which may be a CCD-Camera, Line-Camera, Photomultiplier Tube (PMT), Avalanche Fhotodiode CAPD), CMOS-Camera.

The system, may alternatively and/or additionally comprise other components as would ordinarily be found in fluorescence and wide field microscopes. Examples for means of excitation and detection of fluorescence may be found in: Lakowicz. J. R. Principles of Fluorescence Spectroscopy, Kluwer Academic/Plenum Publishers (1999).

The measurement chamber 82, containing the sample probe (e.g. the sample probe comprising marked particles in a solution), comprises at least an optical transparent site such that the excitation by means of light and the optical detection of the particle properties is possible. The measurement chamber 82 as shown in FIG. 5b comprises preferably an optical transparent cover lid 83 at the upper site. The detections system is preferably placed at an optical transparent site or place of the measurement chamber 82, e.g. the detections system is placed on the upper side of the measurement chamber 82 next to the transparent lid 83.

The measurement chamber 82 is preferably temperature controlled by means of a temperature control system in order to create the desired temperature distribution and/or temperature gradient within the sample probe located in the measurement chamber 82. The measurement chamber 82 is preferably arranged on a substrate 81 to mechanically support the measurement chamber. The measurement chamber preferably comprises a cover lid 83 on the top. A heating structure 91, here in form of a structured layer (e.g. a pattern of a thin gold layer, a thin platinum layer, a thin silver layer) with features in the micrometer scale is arranged such that the sample probe in the measurement chamber 82 can be heated via contact heating, i.e. the heating energy provided by the heating structure 91 is conducted to the sample probe located in the measurement chamber 82. The heating structure 91 may be a structure like it is shown in FIG. 6a, FIG. 6b, FIG. 6c and FIG. 6d. The substrate 81 comprises preferably a defined heat conductivity, and may be made of glass, silicon with an isolating layer, sapphire, diamond, PDMS (Polydimethylsiloxane), plastic, synthetic material, ceramics, metal-ceramic mixture, glass based composite, and/or composite material. The cover lid 83 is preferably optical transparent, preferably thin, and may be made of glass, sapphire, diamond, synthetic material and/or plastic. The heating structure 91 for generating the temperature distribution/gradient is preferably a thin, layer, preferably surrounded by a thin electrical isolating layer 84 (e.g. silicon dioxide). Additionally or alternatively, the heating structure may be embedded in an electrically isolating layer 84 covering the bottom surface or a part of the bottom surface of the measurement chamber. The electrically isolating material is preferably inert to the sample probe. The heating structure 91 may be a structure of copper, gold, silver, platinum, wolfram, or other metals or alloy of metals, composite materials, semiconductors and may also be a structure of electrodes or may also be micro hot plate. Moreover, the heating structure may also be optical transparent.

Moreover, the measurement chamber 82 has preferably a defined height and preferably a defined volume. Preferably the measurement chamber is oriented in a defined angle to the direction of gravitation, more preferably the chamber is oriented to the direction of gravitation in such a way, that thermal convection is minimized. The cover lid 83 may also be temperature controlled.

Moreover the temperature of the measurement chamber 82 may be controlled in such a way that chemical reactions (e.g. PGR, LCR, isothermal PGR, interconversion of chemical substances) can take place.

FIGS. 6*a-c* show a further embodiment according to the present invention in particular preferable two-dimensional structures of the heating structure 91 shown in FIG. 5*a* and 5*b* are shown. All structures comprise a thin narrowing 92 (width d1, preferably 1 μm-100 μm), a preferably thicker feeding structure (width d2, preferably 100 μm-1000 μm) and contact pads for contacting the heating structure with a power supply. The ratio d2/d1>1, preferably d2/d1>>1 more preferably d2/d1>50. The narrowing raises the resistance of the heating structure and thus the temperature rise. In another embodiment the narrowing is expanded to enlarge the area in which a measurement is possible. In FIG. 6*c* a hole 93 is left in the structure. This hole 93 allows, combined with TIRF illumination a fast, detection of thermophoresis in preferably z-direction. As the hole is small (radius of 1 μm to 20 μm) the area in the hole is heated very fast and thus the particles may also move out of the hole fast. This preferably reduces the measurement time.

FIG. 6*d* shows an embodiment with, a multiple arrangement of the heating structures shown, in FIG. 6*a*, FIG. 6*b* and FIG. 6*c*. The six heating structures 91 in FIG. 6*d* are only one possible design but arrangements with 10, 12, 24, 96 or even more heating structures are possible. This multiple arrangement allows measuring many samples at once and thus a measurement time can be saved. The arrangement allows both a parallel measurement and single consecutive measurements.

Figure 7A:
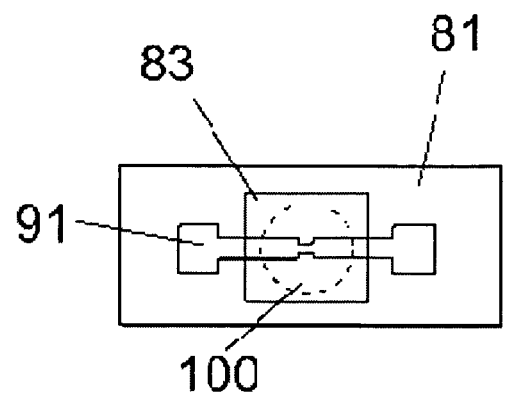
Figure 7B:
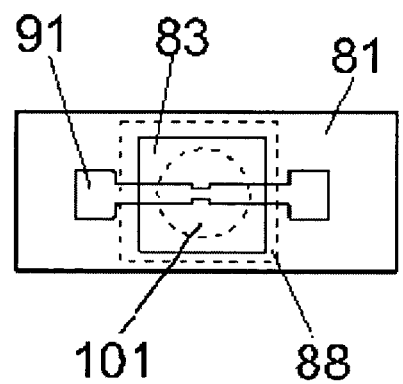
Figure 7C:
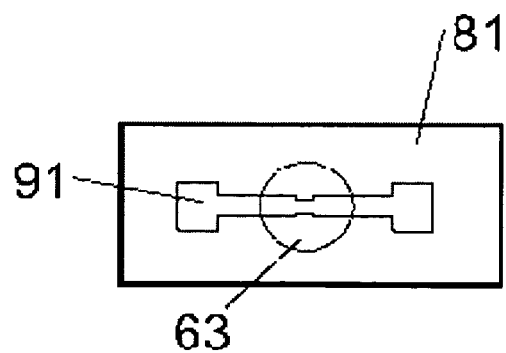

FIG. 7*a-c* show an embodiment of the combination of the heating structure 91 described in FIG. 6*a-c* and FIG. 6*d* and the measurement chamber 82. The heating structure 91 is preferably brought on the substrate 81 using photolithography techniques (e.g. vaporizing the metal on the substrate). The height of the heating structure may lie in the range of 10 nm to 500 nm, preferably in the range of 50 nm to 100 nm. On top of this heating structure an isolating layer can be added (e.g. a silicon dioxide layer of 100 nm to 1000 nm height).

In FIG. 7*a* the substrate 81 contains a recess 100 with a depth of 50 μm to 300 μm. This recess represents the measurement chamber 82 which is sealed with a cover lid 83. It is preferred that the wall of the recess are not completely vertical as the heating structure is vaporized on the substrate and needs to be in electric contact with the contact pads 86 outside the measurement chamber. With inclined walls it is possible to vaporize the metal also on the wall and the connection is created. Like in FIG. 4*a* the height of the hearing structure, is very low and the measurement chamber can be sufficiently sealed without any recess in the cover lid.

FIG. 7*b* shows a further embodiment for combining the heating structures with the measurement chamber 82. The whole measurement device comprises a substrate 81 preferable made of a material with high thermal conductivity e.g. silicon to achieve high temperature gradients, the heating structure 91, a spacer material 88 (e.g. PDMS or a plastic foil with very accurate (+−5 μm) height of 50 μm-300 μm), preferably chemical inert and a cover lid 83. The actual measurement chamber is build using a cut-out 100 in the spacer material. The spacer can comprise a recess for the heating structure at its bottom but as the heating structure is only approximately 50 nm high, spacers without recess also result in a sufficient measurement chamber. The cut-out in the spacer material 88 may be in the range of 0.5 to 10 mm in diameter. The temperature gradient which, can be established in the measurement chamber highly depends on the spacer material and the diameter of the measurement chamber. Thus spacer materials 88 with high thermal conductivity are preferred.

FIG. 7*c* shows a further embodiment for fire heating structures described in FIG. 6*a-c*. The heating structures 91 are placed on the substrate 81. Instead of using a spacer or a recess a droplet of the sample fluid 63 may be placed directly on the heating structure, preferably the droplet 63 is sealed (e.g. with mineral oil, biology grade oil). The Illumination is preferably a TIRF illumination which only excites fluorescence in a very narrow layer parallel to the surface of the substrate. This embodiment allows very quick sample preparations.

Figure 8A:
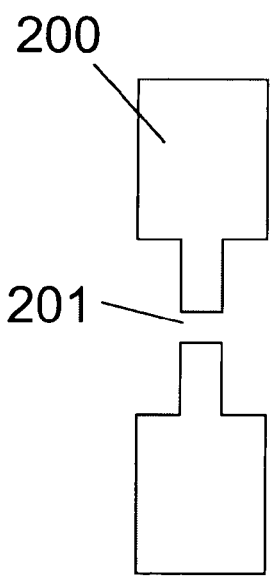

FIG. 8*a* shows a possible embodiment for generating a temperature gradient directly in the fluid using high frequency capacitive heating. Therefore, two electrodes 200 are placed close to each other preferably with a gap 201 between, the electrodes which may lie in the range of 1 μm to 500 μm, more preferably in the range 1 μm to 100 μm. The electrodes comprise a thicker feeding structure (preferable width in the range of 100 μm to 1000 μm) and a thin electrode end (preferable width in the range of 1 μm to 100 μm). The two thin electrode ends are place face to face and the temperature is generated in between. As most current flows the direct way between the electrodes the heating is very constricted to the gap area. Thus, by using very thin electrode ends the heating can be localized to submicron length scales.

Figure 8B:
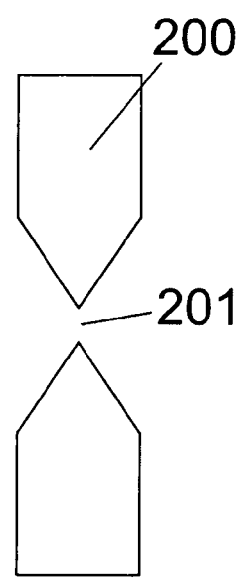

FIG. 8*b* shows a further embodiment of in FIG. 8*a* mentioned heating structure. Again it comprises two electrodes and a gap in between where the heat is generated. In contrast to the embodiment in FIG. 8*a* the thin electrode ends do not have a uniform width but taper towards the gap. This results in high electric fields at the spikes of the electrodes and thus to a more localized heating profile. The width of the thicker feeding structure is preferable in the range of 100 μm to 1000 μm and then tapers off towards the gap.

Figure 9A:
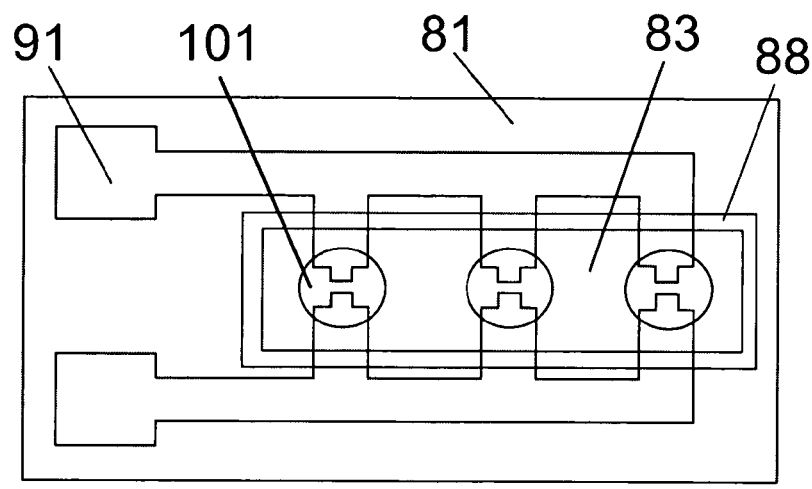
FIGS. 9a-b show an array with three electrical field heating structures in a top view and a cross sectional side view.
Figure 9B:
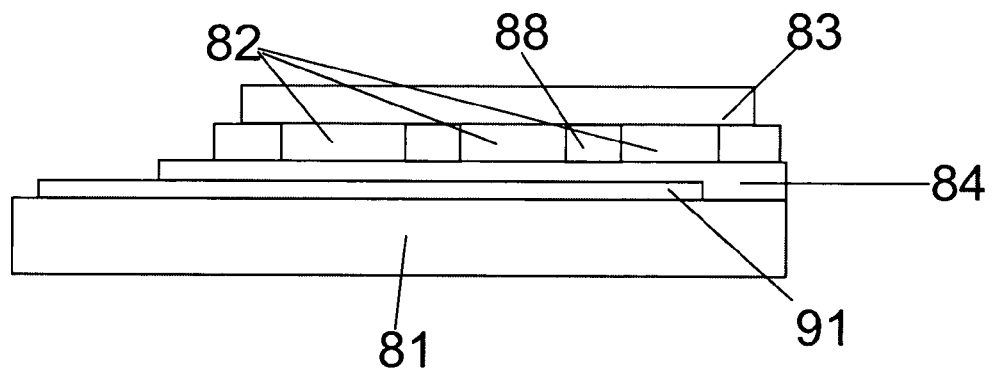

FIG. 9*a-b* show the multiple arrangement of in FIG. 8*a-b* mentioned heating structures. The heating structure is preferably brought on the substrate using photolithography techniques (e.g. vaporizing the metal on the substrate). The height of the heating structure lies in the range of 10 mm to 500 nm, preferably in the range of 50 nm to 100 nm. On top of this heating structure an isolating layer can be added (e.g. a silicon dioxide layer of 100 nm to 100 nm height).

In FIG. 9*a* the structures 91 are placed on a substrate 81, preferably using photolithography techniques. The number of structures placed on one substrate is not limited, so there can be only one heating structure or multiple arrangements of the structure (e.g. 10, 12, 24, 96 or more structure per substrate) placed, on the substrate. The measurement chamber is build using a spacer material 88 containing a cut-out 101 for holding the sample. The height of the spacer is preferably in the range of 50 μm to 300 μm, the cut out has a diameter in the range of 0.5 mm to 5 mm. The spacer material is preferably PDMS or plastic foils with a high thermal conductivity. The measurement chamber 82 is closed with one or multiple cover lids 83 depending on the number of measurement chambers. To simplify contacting the device the thicker feeding structure is widened to a width of 1 mm to 5 mm. This embodiment allows to measure many samples in parallel but with a slightly changed layout (i.e. separating the electrodes on one side) every measurement chamber can be addressed individually and single consecutive measurement can be performed. As it is possible in the embodiment shown in FIG. 7c also here the cover lid can be renounce and the measurement can be perforated in a droplet.

FIG. 9b shows a cross section of FIG. 9a and comprises the substrate 81, any of in FIG. 8a-b shown heating structures, an isolating layer 84, one or multiple measurement chambers 82, the spacer material 88 and a cover lid 83. The isolating layer is preferably made of silicon dioxide or a plastic layer and preferably only 50 to 1000 nm high.

Figure 10:
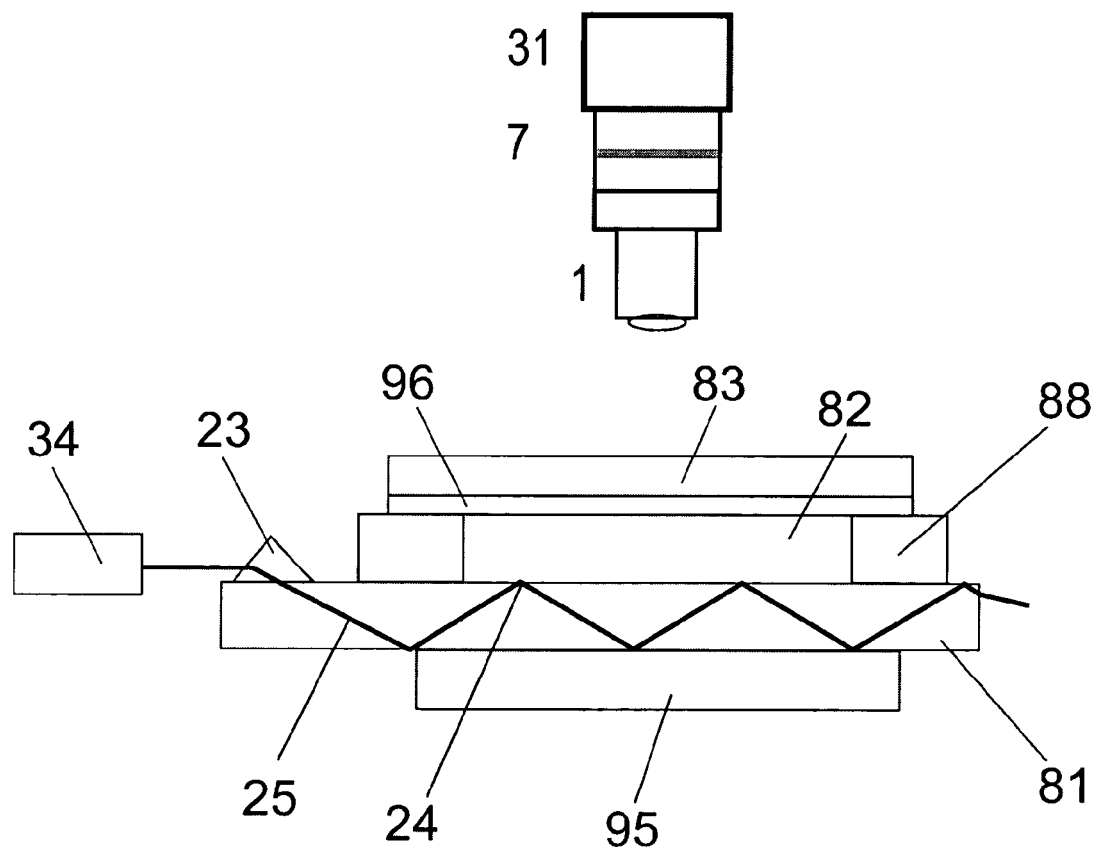
FIG. 10 shows a further embodiment of the present invention with a detection system based on a microscopy setup for the measurement of TIRF.

FIG. 10 illustrates a particular embodiment of a device accordingly to the present invention, in particular a setup for generating a spatial temperature distribution and for measuring the Thermophoresis of marked panicles. The temperature distribution is preferably created parallel to the direction of gravitation. Moreover the side with the greater temperature is preferably the upper side to preferably prevent convection. The detection system may be based on a standard microscopy setup for the measurement of TIRF (total internal reflection fluorescence). The marked particles are preferably excited by means of an evanescent wave and the fluorescence of said particle is preferably detected by a means of detection, preferably a microscope setup containing emission filters. At the surface of the substrate 81 an evanescent wave is created for the local excitation of the fluorescence, preferably in a distance within 150 nm from the surface. The evanescent wave is preferably generated at defined places 24. The TIRF excitation may comprise a light/excitation source 34 and a prism 23. The light/excitation source 34, may be a laser, a fibre coupled laser or a LED. Hie excitation source may also comprise optical elements like lens systems, preferably to provide beam characteristics sufficient for TIRF. The light beam 25 is preferably directed to the interface between the solution of marked particles in the measurement chamber 82 and the substrate 81 by a prism 23 (e.g. a dove prism). Preferably an index of refraction matching oil is placed between prism 23 and substrate 81. At the places 24 the marked particles are excited fluorescently by the generated evanescent wave, allowing for the measurement of the local distribution of the particles near the temperature controlled substrate 81 via TIRF. The fluorescence of said excited particles is preferably detected with a microscope setup comprising an optical lens system 1 which comprises one or more lenses. The optical lens system 1 is preferably an objective 1, e.g. 40×, NA 1.3, oil immersion, ZEISS "Fluar" and an emission filter (band pass/long pass) 7 is preferably arranged between the optical lens system 1 and the detector 31, which may be a CCD-Camera, Line-Camera, Photomultiplier Tube (PMT), Avalanche Photodiode (APD), CMOS-Camera, SPM (silicon multiplier tube).

Moreover the evanescent wave may also be generated at the interface between cover lid 83 and the solution of marked particles in the measurement chamber 82 or at the interface of the, preferably isolated, transparent heating layer 96 (e.g. ITO with an silicon dioxide isolation layer) and the solution of marked particles in the measurement chamber 82.

The measurement chamber 82, containing the solution of the marked particles, is preferably temperature controlled and has preferably a defined height and preferably a defined volume. Preferably the measurement chamber is oriented in a defined angle to the direction of gravitation, more preferably the chamber is oriented to the direction of gravitation in such a way, that thermal convection is minimized, in detail the measurement chamber is placed on or in a substrate 81, preferably an optical transparent substrate, and is covered with a cover lid 83, preferably an optical transparent cover lid. The cover lid 81 may contain, a transparent heating layer 96. Preferably the heating layer 96 is isolated and preferably chemical inert to the solution. The heating layer 96 may be placed at the side of the cover lid 83 which points to the measurement chamber 82 or at the opposite side, pointing to the detection system. The substrate 81 preferably has a defined heat conductivity and may be glass, silicon with an isolating layer, sapphire, diamond, PDMS (Polydimethylsiloxane), plastic, synthetic material, ceramics, metal-ceramic mixture, glass based composite, composite material. The thickness of the measurement chamber 82 may be defined by a spacer 88 (e.g. PDMS, silicon rubber, plastic, synthetic material) and is preferably inert to the solution containing the marked, particles. The temperature of the substrate 81 may be controlled with a heating device 95, e.g. a Peltier element or a water bath or the like.

In the following typical experiments in accordance with the present invention, but not limiting the scope of the invention may be described as follows.

EXAMPLE 1

Determination of Sorer Coefficient in & Setup with a One-Dimensional Temperature Gradient Before an actual measurement the base plate of a measurement chamber is attached to a cooling device and the cap or cover lid of the measurement chamber is attached to the heating element with high thermal conductive glue. These fixings can be permanent or removable, but the glue used for permanent fixing is preferably resistant against solvents like ethanol or isopropanol as the cap and the base plate are preferably cleaned after each measurement.

After fixing the cooling device to the base plate and the heating element to the cap, the chamber confinements are brought onto the base plate. According to a preferred embodiment, the confinements are made of a thin foil or layer with a recess or hole for the chamber. Thus the height of this foil determines the measurement chamber's height. The foil adheres to the base plate and any air enclosed under the foil is removed by pressing the foil to the base before continuing the loading process. If any air is enclosed by the foil foe even height is not assured and the fluid can flow out of the chamber and/or the temperature gradient is not uniform.

In a next step, the solution containing the sample probe with the particles to be measured can be injected hue the recess in the layer. The volume for the measurement is determined by the height of the confinement, and the area or radius of the recess or hole. Normally volumes of 1 µl to a few µl are used.

The measurement chamber is then closed with the cap/cooling device complex which is pressed on the base plate/confinement complex.

Before applying the temperature gradient the fluorescence is measured to obtain the fluorescence intensity of the initial concentration.

In a next step, the temperature gradient is created in the chamber by activating the heating and/or the cooling device. Depending on the dimensions of the chamber and/or the total measurement setup including contact, plates a steady state in temperature is reached after a given time. This time cars be calculated to estimate its influence on the time evolution of the movement of the particles inside the chamber but as the temperature diffusion is about 1000-fold faster than ordinary diffusion this effect can be neglected.

The temperature gradient results in a movement of the solute particles in the chamber, whereas the strength and direction is given by the particles properties. This directed movement leads to change of the concentration profile inside the chamber over the time. The profile is a one-dimensional profile in contrast to the profile obtained by heating the fluid with an IR-Laser beam. This one-dimensional profile allows easier detection methods as no lateral resolution is necessary.

After given time depending on the dimensions of the chamber and the diffusion coefficients of the particles the steady state between thermophoresis and ordinary diffusion is reached. In this steady state the chamber contains different particle concentrations at different heights (z-direction). This profile is now measured using a detection devices with z-resolution.

With an objective with narrow z-focus the focus is moved through the chamber and fee fluorescence intensity is acquired in different z-heights. This intensity values are then plotted over the z-distance and fitted using an exponential function as the concentration profile is given by $c/c0=\exp(-S_T*(T_o-T_u))$. This allows determining the Soret coefficient as the temperatures are detected using thermo elements and/or temperature sensors.

Instead of moving the focus of the objective through the chamber using a confocal microscope, also allows scanning through the sample and acquiring different z-intensities.

The TIRF illumination does not provide the acquisition of a complete z-profile of the concentration. But as only about 100 nm of the chamber are illuminated, and thus contribute to the fluorescence signal it is possible to obtain the concentration evolution in this region over time. After acquiring both the thermophoretic movement of the sample and the back diffusion the diffusion, coefficient and the Soret coefficient are determined and thus the sample's size and surface properties.

EXAMPLE 2

Determination of Soret Coefficient in a Setup with a Vertical Heating Structure

Step 1a, Background Measurement:

A sample buffer (sample probe) without fluorescently marked sample molecules-particles is filled in a microfluidic chamber containing a central heating wire which is parallel to the direction of the fluorescence detection. The heating wire is positioned in the center of the chamber and extends through the wall of the microfluidic chamber. The wire is preferably fixed to the chamber wall by glue, which is resistant to water and organic solvents. After a few microliter of the sample solution containing only buffer is filled into the chamber, it is sealed by putting a cover lid on the opening on top. The height of the chamber (i.e. in direction of the heating wire; distance between cover slip and the bottom plate) is less than 500 μm preferably less than 100 μm and care should be taken that the height of the chamber is the same if results measured in different chambers are compared. The chamber is placed on a device for fluorescence excitation and detection (e.g. a fluorescence microscope). The wire is connected to a current source and the focus of the microscope objective is set on the chamber by using a 50/50 beamsplitter and residual light from the surrounding or the light source at low power. The fluorescence of the sample buffer is measured, while the excitation light source is turned on. This way the background value by e.g. light scattering and auto fluorescence is obtained.

Step 1b, Determination of Fluorescence Level Before Heating by the Conducting Wire:

An (aqueous) solution of a fluorescently labelled sample (e.g. biomolecules, nanoparticles, microbeads which have an affinity for other molecules) is filled in the microfluidic chamber described in Step 1a. This might be the same chamber where the first sample has been removed, or a new microfluidic chamber. Fluorescence is exited and the focus of the objective is set on the chamber. Then fluorescence is excited and recorded with (CCD-Camera) or without (Photomultiplier tube. Avalanche Photodiode) spatial resolution for less than 10 seconds on a CCD device or photomultiplier with exposure times of 25 milliseconds up to 1 second. Then the fluorescence excitation is turned off. The sample is positioned relative to the CCD camera in such a way that at least part, of the wire is observed in the image.

Step 2, Starting of Heating, by the Conducting Wire:

In the following the hearing by the conducting wire, is turned on by turning on a DC-current and a spatial temperature distribution is established around the wire within the solution. In this case for a 1 cm (diameter 50 μm) wire a potential of 20 mV is used to obtain an increase in temperature of 4° C. The power needed depends on the thickness/length of the wire and the temperature gradient needed for the experiment. The temperature gradient has been calibrated once and it is not necessary to repeat this, calibration every time an experiment is performed. It is of advantage that in the experiment the decrease of fluorescence due to photobleaching is lower than 5%.

The maximal temperature elevation is below the temperature which causes damage to the molecules in the solution or alters their interaction (e.g. temperatures between 1 and 5° C. above ambient temperature). In the experiment described here the heating prevailed for 200 seconds.

Step 3, Recording of the Spatial Fluorescence (i.e. Concentration) Profile:

After this period of time the fluorescence excitation is turned on and images are recorded with the same frame rate and length as described in step 1b. Step 3 is the last acquisition step necessary for evaluation of thermo-optical properties.

For determination of the Soret coefficient the spatial temperature distribution should be known. Therefore the protocol described above is preferably performed with a temperature sensitive fluorescent dye whose fluorescence dependence on temperature has been calibrated once shows a fluorescence change with temperature. The temperature distribution may have been measured once and can be assumed to be the same as long as the dissipated power is not changed.

Processing the Raw Data:

In many cases a bleaching correction is necessary. For a linear bleaching correction it is necessary to wait for the back-diffusion of all molecules following the end of step 3. This increases the time consumption of the analysis. For precise and last measurements it is of advantage to determine the strength of bleaching from image to image and correct every individual image with, its own bleaching factor. For a precise bleaching correction, a point as far away from the heating wire as possible is chosen. In case fluorescence is recorded without spatial resolution (e.g. avalanche photodiode or photomultiplier) photo-bleaching is corrected best by determining once the bleaching characteristic of a certain dye without heating current turned on in a control experiment. The images from step 1a are subtracted from the images taken in step 1b and 3.

The images taken in step 1b are preferably used to correct all images for inhomogeneous illumination.

Data Evaluation:

The center of the wire is chosen and the fluorescence distribution of the molecules of interest is radially averaged. The same average procedure is performed with the temperature measurement. The temperature dependence is used to calculate the temperature increase as a function of the distance from the heated wire. The fluorescence distribution of the molecule of interest (sample) is corrected for the fluorescence temperature dependence of the marked molecule. This way the concentration profile is obtained. The temperature at a certain radius can now be compared to the concentration. The Soret coefficient is obtained by the following relation; $c/c0=\exp-ST(T-T0)$, where c/c0 is the relative concentration with heating and T–T0 is the temperature difference.

EXAMPLE 3

Determination of Hydrodynamic Radius in a Setup with a Vertical Heating Structure The thermo-optical characterization method allows also to quantify the hydrodynamic radius of proteins/nanoparticles and even more important of complexes of biomolecules (which are not connected covalently to each other). Thermophoresis provides a comparably robust and precise way to measure the hydrodynamic radius of molecules from less than a nanometer up to a few microns. This thermo-optical characterization method can also be used in complex fluids as there are to mention blood, blood serum and cell lysate fox example, in which state of the art techniques face problems Data Acquisition:
A typical measurement can be described as follows:
Step 1:
A solution of fluorescently labeled molecules (e.g. Quantum dots; excitation 480 nm, emission 650 nm) is filled into a microfluidic measurement, chamber containing a vertical, heating wire (parallel to the direction of fluorescence detection). The microfluidic chamber with, a height of 100 μm is sealed with a cover lid and placed on a device for fluorescence detection. The ends of the heating wire are connected to a power source. Fluorescence is excited and the focus of the objective is set into the chamber.

Fluorescence is excited and recorded with spatial resolution, for less than 5 seconds on a CCD device with a frame rate, which is in the range of 100 Hz to 0.2 Hz. These image(s) provides the necessary information about the fluorescence level at 100% concentration. Then fluorescence excitation is turned off.

Step 2:
The current through the 50 μm heating wire is turned on (i.e. approx 20 mV potential on a wire with a length of 1 cm to obtain, a temperature maximum of 4° C.). The established local spatial temperature distribution causes the molecule drift to lower or higher temperatures, depending on the particular molecule to be analyzed. Depending on the size of the wire and the maximum temperature the heating wire creates temperature gradients between 0.01 and 0.1 K/μm. The temperature gradient has been calibrated once and it is not necessary to repeat this calibration every time an experiment, is performed. Depending on the thermophoretic properties of the molecules in the solution (i.e. if they move fast in a thermal gradient or slow) the current is turned on as long as necessary to obtain a substantial change of the spatial concentration distribution (here: for 5 seconds up to 100 seconds). In practice 10% of change in concentration should be achieved and in cases that the thermophoretic properties allow only less than 10% concentration change, the heating should continue until the steady state (i.e. maximum depletion or accumulation) is reached. After this period of time the heating is turned off.

Step 3:
The same time the heating current is turned off, the fluorescence excitation is turned on and the emission is recorded with the same frame rate used in the first step of fluorescence imaging. This time the redistribution of the molecules is imaged for 5 seconds up to 50 seconds. The exact time depends on the velocity with which the molecules diffuse (i.e. the tune it takes them to equalize 90% of the concentration gradient established by thermophoresis). The frame rate is dependent on the strength of change in concentration achieved and the size of the molecules, in this experiment quantum dots (radius of 12 ran) showed more than 30% depletion. In this case a frame rate of 20 Hz was used.

Data Processing—Photobleaching:
The fluorescence, images are preferably corrected for photobleaching. Since there is essentially no spatial temperature profile in the solution while fluorescence images are taken, the bleaching correction is possible with high precision, (i.e. the rate of photobleaching is temperature dependent).

For correction the fluorescence at an edge of the measurement chamber (i.e. a spot as far away from the heated wire as possible), where thermophoresis during step 3 is negligible is evaluated to determine the photobleaching. If photobleaching is present, the fluorescence will decrease from image to image. The individual, factor for each image is used to correct the images for bleaching. Another possibility is to calculate the bleaching for every single pixel from the images taken in Step 1. The bleaching rate per pixel can be used to correct every pixel, from step 3 images for the photobleaching effect.

Data Processing—Inhomogeneous Illumination Correction and Normalization to 100% Concentration:
Preferably, all images taken in step 3 are divided by a single or an average image taken in step 1 and multiplied by 100. This way a correction for inhomogeneous illumination is achieved and the fluorescence is normalized to 100% concentration.

Data Processing—Determining the Hydrodynamic Radius:
From the first image of the step 3 image series the concentration distribution is extracted (preferably an image is taken were the spatial temperature distribution has vanished). A software tool evaluates the Diffusion coefficient (or multiple Diffusion coefficients in case of a mixture) by relating the experimentally measured relaxation of the concentration gradient to data obtained by a numerical simulation. Using the Stokes-Einstein relation the hydrodynamic radius is inferred from the diffusion coefficient.

EXAMPLE 4

Measuring the Binding Interaction of BSA (Bovine Serum Albumin) with Fluorescent Nanoparticles Using Beating Structure with TIRF Illumination A further preferred experiment for the herein presented invention is to determine the binding interaction of a nonfluorescent protein and fluorescently marked particle. This can be done using a change in the size (i.e. the hydrodynamic radius) of labeled particle due to the interaction with its binding partner. The typical measurement procedure can be described as follows:

Step 1: Sample Preparation
To determine the unspecific binding of proteins to nanoparticles a titration experiment is performed. Therefore, different samples are prepared containing nonfluorescent BSA in 1×PBS buffer at different concentrations (e.g. 0 nM-0.1 nM, 1 nM, 2 nM, 10 nM, 100 nM, 500 nM, 1 μM, 2 μM, 5 μM, 10 μM) each mixed with the fluorescent nanoparticle (e.g.; 10 nm radius with excitation; 535 nm, emission: 575 nm (Nile red)) at constant concentration (150 nM).

Step 2: Loading and Calibrating the Device

After preparing these samples the measurement chambers of a multi-well device with 12 measurement chambers are loaded with the samples and one measurement chamber with buffer only. Then the chamber is closed with the cover lid. The device is connected to a switched-off current, source and is placed in the illumination and detection unit to provide fluorescence excitation and detection. The illumination is performed using a green laser (wavelength: 532 nm) coupled into the substrate with a TIRF prism on top of the substrate. The resulting illumination inside the measurement chamber is achieved by the evanescent field which penetrates about 100 nm into the chamber. This way the fluorescence is only excited and detected in the region of the heating structure and background fluorescence is minimized.

The illumination and detection are calibrated, i.e. the heating structure is in the focus of the detection unit and the laser creates a TIRF illumination whereas the images can either contain just one heating spot with a high spatial resolution or all hearing spots in one images which allows to speed up the analysis of images.

Step 3: Data Acquisition:

Now some dark images (5-10 images) without any illumination are taken to determine the background.

Then the TIRF illumination is switched on and the fluorescence intensity (COLD images) is measured (a time series with 5-10 images). To avoid photobleaching the TIRF illumination is then switched off again. Now the electric current is switched on and the heating structure is heated with a voltage of 1 mV.

This local temperature distribution leads to a thermophoretic depletion of the nanoparticles. After a heating time of 1 μs-10 min the TIRF illumination is switched on again and the electric current is switched off. Then a time series to determine the back diffusion is taken. For this time series the frame rate for acquiring the series should be fast (e.g. 10 Hz for 10 nm QuantumDots or 40 Hz for proteins).

Step 4: Data Processing—Photobleaching:

The second image series is now analyzed to obtain, the diffusion coefficient of the particles. Therefore the complete series is corrected by background subtraction. The COLD images are then analyzed, to calculate a correction for the effect of photobleaching which is assumed to be linear in time. This linear decrease is later used to correct the time evolution of the back diffusion (as an alternative a photobleaching rate can be determined for every single image. Therefore fluorescence is detected at a point where the effect of the temperature gradient is negligible).

Step 5: Data Processing—Backdiffusion:

Now the corrected fluorescence intensity during the back diffusion of an area close to the heating structure is plotted over time. To obtain the diffusion coefficient from this plot the measurement chamber is simulated using a finite element solver with varying diffusion coefficients D and the quadratic error of the fitting curve is minimized. Repeating this process results in the exact diffusion coefficient and thus in the hydrodynamic radius of the particles.

The last step of analyzing the corrected fluorescence intensity to obtain the diffusion coefficient is repeated for all 12 measurement spots on the multi-well device. Finally the measured hydrodynamic radii which are calculated over the Stokes-Einstein-relation are plotted over the BSA concentration.

Due to the parallel heating of the samples the electric measurement saves measurement time and allows the acquisition of a complete titration experiment in about 15 minutes.

EXAMPLE 5

Detection of Interactions in a Setup with a Vertical Heating Structure

The thermo-optical characterization provides the means for fast analysis of biomolecule interaction. The term interaction comprises interaction between biomolecules (e.g. protein, DNA, RNA, hyaluronic acids etc) but also between modified nanoparticles/micro beads/Ions and biomolecules. A typical experiment to detect/quantify interactions can be described as follows:

Step 1a, Background Measurement:

The sample buffer without fluorescently labelled sample molecules/particles is filled in a microfluidic chamber containing a central heating wire which is parallel to the direction of the fluorescence detection. The chamber is sealed with a cover slip. The height of the chamber (i.e. in direction of the heating wire) is less than 500 μm in this case less than 100 μm and care should, be taken, that the height of the chamber is reproducible if results are compared. The chamber is placed an a device for fluorescence excitation, and detection (e.g. a fluorescence microscope). The wire is connected to a current, source and the focus of the microscope objective is set on the chamber by using a 50/50 beamsplitter and residual light from the surrounding or the light source at low power. The fluorescence of the sample buffer is measured) while the excitation light source is turned on. This way the background value is obtained which arising from e.g. light scattering and auto fluorescence.

Step 1b, Determination of Fluorescence Level before Heating by the Conducting Wire:

An aqueous solution of a fluorescently labelled sample (e.g. biomolecules, nanoparticles, microbeads which have an affinity for other molecules) is filled in the microfluidic chamber described in Step 1a. Fluorescence is exited and the focus of the objective is set into the chamber.

Then Fluorescence is excited and recorded with (CCD-Camera) or without (Photomultiplier tube. Avalanche Photodiode) spatial resolution for less than 10 seconds on a CCD device or photomultiplier with exposure times of 25 milliseconds up to 1 second. Thereafter the fluorescence excitation is turned off.

Step 2, Starting of Beating by the Conducting Wire:

In the following the heating by the conducting wire is turned on by turning on a DC current and a spatial temperature distribution is established around the wire within the solution, in this case for a 1 cm long (diameter 50 μm) wire a potential of 20 mV is used to obtain an increase in temperature of 4° C. The power needed depends on the thickness/length of the wire and the temperature gradient needed for the experiment. The temperature gradient has been calibrated once and it is not necessary to repeat, this calibration every time an experiment is performed.

The maximal temperature induced in the experiment is below the temperature which causes damage to the molecules in the solution or alters their interaction behaviour (e.g. temperatures between 1 and 5° C. above ambient temperature). In the experiment described here the heating prevailed for 200 seconds.

Step 3, Recording of the Spatial Fluorescence (i.e. Concentration) Profile:

After this period of time the fluorescence excitation is turned on and images are recorded with the same frame rate and length as described in step 1b. Step 3 is the last acquisition-step necessary for evaluation of thermo-optical properties.

For quantification of interactions the protocol described previously is performed with additional samples. Step 1b to step 3 is repeated with solutions of the fluorescently labelled sample (e.g. protein) at the same concentration which is mixed with a varying amount of the binding partner with which the interaction quantified. The number of samples in the titration series determines how often, step 1b, step 2 and step 3 are repeated (i.e. how often a new chamber is filled with a sample). If the strength of the interaction should be quantified in terms of a dissociation or association constant ($K_d$, $K_a$), than the procedure described previously has to be conducted with varying concentrations of binding partner (e.g. 0.01×-10× the concentration of the fluorescently labelled binding partner). This means that a titration of binding partner should be performed. For the qualitative detection of an interaction (i.e. not detecting the strength of interaction) it is necessary to mix the fluorescently labelled sample with a sufficient amount, of binding partner (or unknown sample) so that a substantial, amount of the fluorescently labelled molecule is assumed to be in complex with the binding partner.

Processing the Raw Data;

For a linear bleaching correction it is necessary to wait for the back-diffusion of all molecules following the end of step 3. This increases the time consumption of the analysis. For precise and fast measurements it is of advantage to determine the strength of bleaching from image to image and correct every individual image with its own bleaching factor. For a precise bleaching correction it is important that the temperature gradient at distance from the heat, spot is low (e.g. below 0.0001 K/μm). In case fluorescence is recorded without spatial resolution (e.g. avalanche photodiode or photomultiplier) photo-bleaching is corrected best by determining the bleaching characteristic of a certain dye once without heating in a control experiment.

The images taken in step 1b are used to correct all images for inhomogeneous illumination.

Data Evaluation:

Qualitative detection of interaction (i.e. detecting if a certain molecule is present in a solution): From the image series the spatial fluorescence distribution of the reference experiment (i.e. fluorescently labelled molecule/particle without binding partner) and a second experiment (i.e. were the binding partner is present) is extracted. The fluorescence is plotted versus the distance from the heat spot and pixels with the same temperature (i.e. same distance from heating wire) are averaged. The spatial concentration distribution is obtained by correcting the fluorescence intensities for the respective temperature dependence of the dye. For the qualitative detection of interaction as well as the quantification of the interaction strength a correction for temperature dependency is not necessary, and the spatial fluorescence distribution is sufficient. This enables us to use any fluorescent dye on the market without characterization of its temperature dependency.

The values of the fluorescence profile are integrated up to the distance where the temperature is below 10% of the maximum temperature (e.g. 70 μm). The integrated, values are compared and a change give a precise indication if there is an affinity between the substances at the concentrations used, since the interaction changes; the thermo-optic properties (e.g. thermophoretic mobility, surface size and chemical groups on surface). In most cases the interaction between proteins leads to higher fluorescence (concentration) at higher temperatures. In case that a detector with no spatial resolution, is used, no integration is necessary.

In general if more than a single frame is recorded in step 1b and 3 an integration of multiple frames is possible.

For a quantification of affinities the same procedure is performed for all experiments at various concentrations of the non fluorescent binding partner. The result of the integration for the reference experiment (i.e. without binding partner) is subtracted from the integrated values obtained for the different concentrations of binding partners. From this evaluation one gets the amount of interacting complexes in arbitrary units. By dividing the values by the value were binding is saturated the relative amount of complexes at a certain concentration of the binding partner is obtained. From this dataset also the concentration of free binding partner (i.e. non fluorescent) can be determined and the strength of the interaction can be quantified in terms of association or dissociation constant.

The invention claimed is:

1. A method of measuring the thermophoretic characteristics of particles in a solution comprising the steps of:
    (a) providing a sample probe comprising marked particles in a solution;
    (b) providing a temperature control system for creating a temperature gradient within said sample probe by contact heating, electrical heating and/or cooling;
    (c) detecting the marked particles at a first time;
    (d) creating a temperature increase of from 0 to about 5 K and a temperature gradient of 0-20 K/μm within the sample probe by means of the temperature control system;
    (e) detecting the marked particles in the sample probe at a second time and/or at a predetermined location within the temperature gradient, and
    (f) characterizing the particles based on said two detections.

2. The method of claim 1, wherein said detecting the marked particles occurs at a predetermined second time.

3. The method according to claim 1, further comprising the step of performing a third detection at a third time.

4. The method of claim 3, wherein said third detection is performed at a predetermined third time.

5. The method of claim 1, wherein the second time and/or third time is while and/or after heating.

6. The method of claim 5, wherein the first, second and/or third times are predetermined times.

7. The method of claim 6, wherein the predetermined times are determined based on absolute time, the completion or conduction of further method steps, and/or relative time between the two times.

8. Method according to claim 1, further comprising the step of exciting luminescence of said marked particles wherein the detection steps comprise detecting luminescence of said excited particles.

9. The method of claim 8, wherein said luminescence is fluorescence.

10. Method according to claim 1, wherein the temperature control system controls the temperature by a heating means and/or cooling means using one or more of a wire, a Peltier element, a plate, a conductive path, means for creating a high frequency electric field in the sample probe, an indium-tin-oxide (ITO) element and/or means with a radiation absorbing surface.

11. Method according to claim 1, wherein detection is performed by use of one or more of epifluorescence (EPI) microscope, total internal reflection fluorescence (TIRF) microscope, confocal microscope, CCD, APD, PMT, and/or a microscope.

12. Method according to claim 1, wherein the temperature gradient lies in the range from about 0.01 K/μm to 0.1 K/μm.

13. Method according to claim 1 wherein the sample probe volume lies in the range from about 1 pl to 100 µl.

14. Method according to claim 1, wherein the time span between the first time and the second time is less than 5 minutes.

15. Method according to claim 1, wherein the predetermined location within the temperature gradient is at the surface, the bottom, the side of a measurement chamber and/or the sample probe and/or at a predetermined distance from heating and/or cooling means or at a place of specific temperature.

16. The method of claim 15, wherein the predetermined location is close to the heating and/or cooling means or near a surface in a region of high temperature gradients.

17. Method according to claim 1, wherein a plurality of sample probes are measured subsequently and/or in parallel.

18. A device for measuring thermophoretic characteristics of particles in a solution according to the method of claim 1, the device comprising:
  a measurement chamber for receiving a sample probe containing marked particles in a solution;
  means for detecting the marked particles in the sample probe;
  a temperature control system for creating a temperature increase of from 0 to about 5 K and a temperature gradient of 0-20 K/µm within said sample probe by contact heating and/or cooling, and
  a control means adapted for controlling said detection means to detect the marked particles at a first time and for controlling said detection means and temperature control system to detect the marked particles in the sample probe at a second time and/or at a predetermined location within a temperature gradient created by the temperature control system.

19. Device according to claim 18, wherein the control means is adapted to control the first and/or second times to be predetermined times.

20. Device according to claim 18, further comprising means for exciting luminescence of said marked particles wherein the detection means is adapted to detect luminescence of said excited particles.

21. Device according to claim 18, wherein the temperature control system comprises one or more of each or more of the following heating and/or cooling means: a wire, a Peltier element, a plate, a conductive path, means for creating a high frequency electric field, an indium-tin-oxide (ITO) element and/or means with a radiation absorbing surface for controlling the temperature.

22. Device according to claim 18, wherein the detection means comprises one or more of epifluorescence (EPI) microscope, total internal reflection fluorescence (TIRF) microscope, confocal microscope, CCD, APD, PMT, and/or a microscope.

23. Device according to claim 18, wherein the device comprises means for characterizing the particles based on said detections.

24. Device according to claim 18, wherein the temperature control system is adapted to create a temperature gradient lying in the range from about 0.01 K/µm to 0.1 K/µm.

25. Device according to claim 18, wherein the device is adapted to receive a sample probe having a volume lying in the range from about 1 pl to 100 µl.

26. Device according to claim 18, wherein control means is adapted to control the time span between the first time and the second time is less than 5 minutes.

27. Device according to claim 18, wherein the detection means is adapted to conduct the detection at the surface, the bottom, the side of the measurement chamber or the sample probe and/or at a predetermined distance from heating means or at a place of specific temperature.

28. Device according to claim 18, wherein the device is adapted to measure a plurality of sample probes subsequently and/or in parallel.

29. Device according to claim 18, wherein the device comprises a substrate containing a measurement chamber for receiving the sample probe.

30. Device according to claim 18, wherein the measurement chamber and/or the sample probe is covered by a cover lid.

31. Device according to claim 30, wherein the cover lid comprises one or more filling holes and/or pin holes.

32. Device according to claim 18, wherein the measurement chamber is defined as a recess in a substrate.

33. Device according to claim 18, comprising filling holes for filling the measurement chamber.

34. Device according to claim 18, wherein one or more of the heating and/or cooling means of the temperature control system extend into and/or through the measurement chamber and/or the sample probe.

35. Device according to claim 18, wherein one or more of the heating and/or cooling means of the temperature control system contacts the measurement chamber and/or the sample probe.

36. Device according to claim 18, wherein one or more of the heating and/or cooling means are electrically isolated vis-à-vis the measurement chamber and/or the sample probe.

37. The device according to claim 36, wherein one or more of the heating and/or cooling means are electrically isolated vis-à-vis the measurement chamber and/or the sample probe by an electrical isolation coating and/or an electrical isolation layer.

38. Device according to claim 18, wherein the measurement chamber and/or the sample probe is covered by a cover lid and wherein the cover lid is a heating and/or cooling element.

39. Device according to claim 38, wherein the cover lid is an ITO element.

40. Device according to claim 18, wherein the measurement chamber is defined by a structured surface and/or the sample probe is positioned on a surface of a substrate as a droplet, and where the heating and/or cooling element is defined by/on/in the substrate on which the droplet is placed.

41. A method to measure thermophoretic characteristics of particles in a solution by using a device according to claim 18, comprising:
  (a) providing a sample probe comprising marked particles in a solution;
  (b) providing a temperature control system for creating a temperature increase of from 0 to about 5 K and a temperature gradient of 0-20 K/µm within said sample probe by contact heating, electrical heating and/or cooling;
  (c) detecting the marked particles at a first time;
  (d) creating a temperature gradient within the sample probe by means of the temperature control system;
  (e) detecting the marked particles in the sample probe at a, preferably predetermined, second time and/or at a predetermined location within the temperature gradient, and
  (f) characterizing the particles based on said two detections.

* * * * *